(12) United States Patent
Jo

(10) Patent No.: US 10,445,266 B2
(45) Date of Patent: Oct. 15, 2019

(54) ELECTRONIC DEVICE AND METHOD FOR PREVENTING CORROSION TO CONNECTOR

(71) Applicant: Samsung Electronics Co., Ltd., Suwon-si, Gyeonggi-do (KR)

(72) Inventor: Yeon-Rae Jo, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/850,477

(22) Filed: Dec. 21, 2017

(65) Prior Publication Data

US 2018/0181509 A1 Jun. 28, 2018

(30) Foreign Application Priority Data

Dec. 23, 2016 (KR) ........................ 10-2016-0178383

(51) Int. Cl.
| | |
|---|---|
| *G01N 27/06* | (2006.01) |
| *G06F 13/24* | (2006.01) |
| *G06F 13/42* | (2006.01) |
| *G06F 13/40* | (2006.01) |
| *G06F 13/38* | (2006.01) |
| *H04N 5/232* | (2006.01) |
| *H04N 5/225* | (2006.01) |
| *G03B 17/08* | (2006.01) |
| *G01N 27/04* | (2006.01) |

(52) U.S. Cl.
CPC ............ *G06F 13/24* (2013.01); *G01N 27/06* (2013.01); *G06F 13/385* (2013.01); *G06F 13/4068* (2013.01); *G06F 13/4282* (2013.01); *H04N 5/2257* (2013.01); *H04N 5/23245* (2013.01); *G01N 27/048* (2013.01); *G03B 17/08* (2013.01); *G06F 2213/0042* (2013.01); *G06F 2213/2424* (2013.01); *H04N 5/232411* (2018.08)

(58) Field of Classification Search
CPC ...... H04N 5/2257; G03B 17/08; G01N 27/06; G01N 27/048; G01N 17/02; G01N 17/04
See application file for complete search history.

(56) References Cited

U.S. PATENT DOCUMENTS

| | | | |
|---|---|---|---|
| 2011/0228075 A1* | 9/2011 | Madden ................ | G03B 15/05 348/81 |
| 2016/0268726 A1 | 9/2016 | Chong et al. | |
| 2017/0344508 A1* | 11/2017 | Setiawan ............ | G06F 13/4282 |

* cited by examiner

*Primary Examiner* — Ernest Unelus
(74) *Attorney, Agent, or Firm* — Jefferson IP Law, LLP

(57) ABSTRACT

An electronic device and method for communicating with an external electronic device that is connected via a connector of the electronic device are provided. The electronic device includes a connector including a first pin and a second pin, a communication interface connected with the connector, and at least one processor electrically connected with the communication interface, wherein the at least one processor may be configured to apply a first current to the first pin, determine whether liquid is introduced into the connector using the second pin, and if the liquid is introduced into the connector, apply a second current smaller than the first current to the first pin.

17 Claims, 10 Drawing Sheets

ELECTRONIC DEVICE AND METHOD FOR PREVENTING CORROSION TO CONNECTOR

CROSS-REFERENCE TO RELATED APPLICATION(S)

This application claims the benefit under 35 U.S.C. § 119(a) of a Korean patent application filed on Dec. 23, 2016 in the Korean Intellectual Property Office and assigned Serial number 10-2016-0178383, the entire disclosure of which is hereby incorporated by reference.

TECHNICAL FIELD

The present disclosure relates to electronic devices. More specifically, the present disclosure relates to electronic devices and methods for preventing corrosion to the connectors of the electronic devices.

BACKGROUND

Recently, electronic devices are providing more diversified services and additional functions. To meet users' various needs and raise use efficiency of electronic devices, communication service carriers or device manufacturers are jumping into competitions to develop electronic devices with differentiated and diversified functionalities.

As the technology of electronic devices advances, data communication services are vigorously provided through wired connections between electronic devices and computers or external devices. A cable may electrically be connected with a charger for electronic devices. For example, the connector of an electronic device may be a universal serial bus (USB) connector. The connector may be intended for data input and output or charging a wireless terminal. The connector may include a socket provided in the electronic device and a plug connector for connection with a cable. The electronic device may transmit content through the USB connector to an external electronic device. As the electronic device and the electronic device are connected together via the USB connector, they may be defined as a host and a device, respectively.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide an electronic device and method for preventing corrosion to the universal serial bus (USB) connector of the electronic device.

In accordance with an aspect of the present disclosure, an electronic device is provided. The electronic device includes a connector including a first pin and a second pin, a communication interface connected with the connector, and at least one processor electrically connected with the communication interface, wherein the at least one processor may be configured to apply a first current to the first pin, determine whether liquid is introduced into the connector using the second pin, and if the liquid is introduced into the connector, apply a second current smaller than the first current to the first pin.

In accordance with another aspect of the present disclosure, a method for preventing corrosion to a connector in an electronic device is provided. The method includes applying a first current to a first pin of the connector, determining whether liquid is introduced into the connector using a second pin of the connector, and when the liquid is introduced into the connector, applying a second current smaller than the first current to the first pin.

In accordance another aspect of the present disclosure, an electronic device is provided. The electronic device includes a connector for connecting with an external electronic device, the connector including at least one pin capable of detecting a contact of a designated substance and a detecting circuit capable of detecting whether at least part of the designated substance contains a substance different from the designated substance through the at least one pin.

According to various embodiments of the present disclosure, there may be provided an electronic device and method for preventing corrosion to the USB connector of the electronic device.

In accordance with another aspect of the present disclosure, an electronic device having a USB type-C connector is provided. The electronic device includes a communication interface including the USB type-C connector and at least one processor electrically connected with the communication interface. The at least one processor may apply a first current to a first pin of the USB type-C connector in a low-power mode, determine whether an interrupt occurs in the USB type-C connector based on at least one second pin of the USB type-C connector, determine whether the interrupt is caused by the inflow of liquid into the USB type-C connector, and maintain the low-power mode upon determining that the liquid has been introduced.

According to an embodiment of the present disclosure, a method for preventing corrosion to an electronic device having a USB type-C connector may comprise applying a first current to a first pin of the USB type-C connector in a low-power mode, determining whether an interrupt occurs in the USB type-C connector based on at least one second pin of the USB type-C connector, determining whether the interrupt is caused by the inflow of liquid into the USB type-C connector, and maintaining the low-power mode upon determining that the liquid has been introduced.

According to an embodiment of the present disclosure, a computer-readable storage medium storing a program including commands for preventing corrosion to an electronic device having a USB type-C connector may comprise a first command set for applying a first current to a first pin of the USB type-C connector in a low-power mode, a second command set for determining whether an interrupt occurs in the USB type-C connector based on at least one second pin of the USB type-C connector, a third command set for determining whether the interrupt is caused by the inflow of liquid into the USB type-C connector, and a fourth command set for maintaining the low-power mode upon determining that the liquid has been introduced.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, like reference numerals will be understood to refer to like parts, components, and structures.

DETAILED DESCRIPTION

Figure 1:
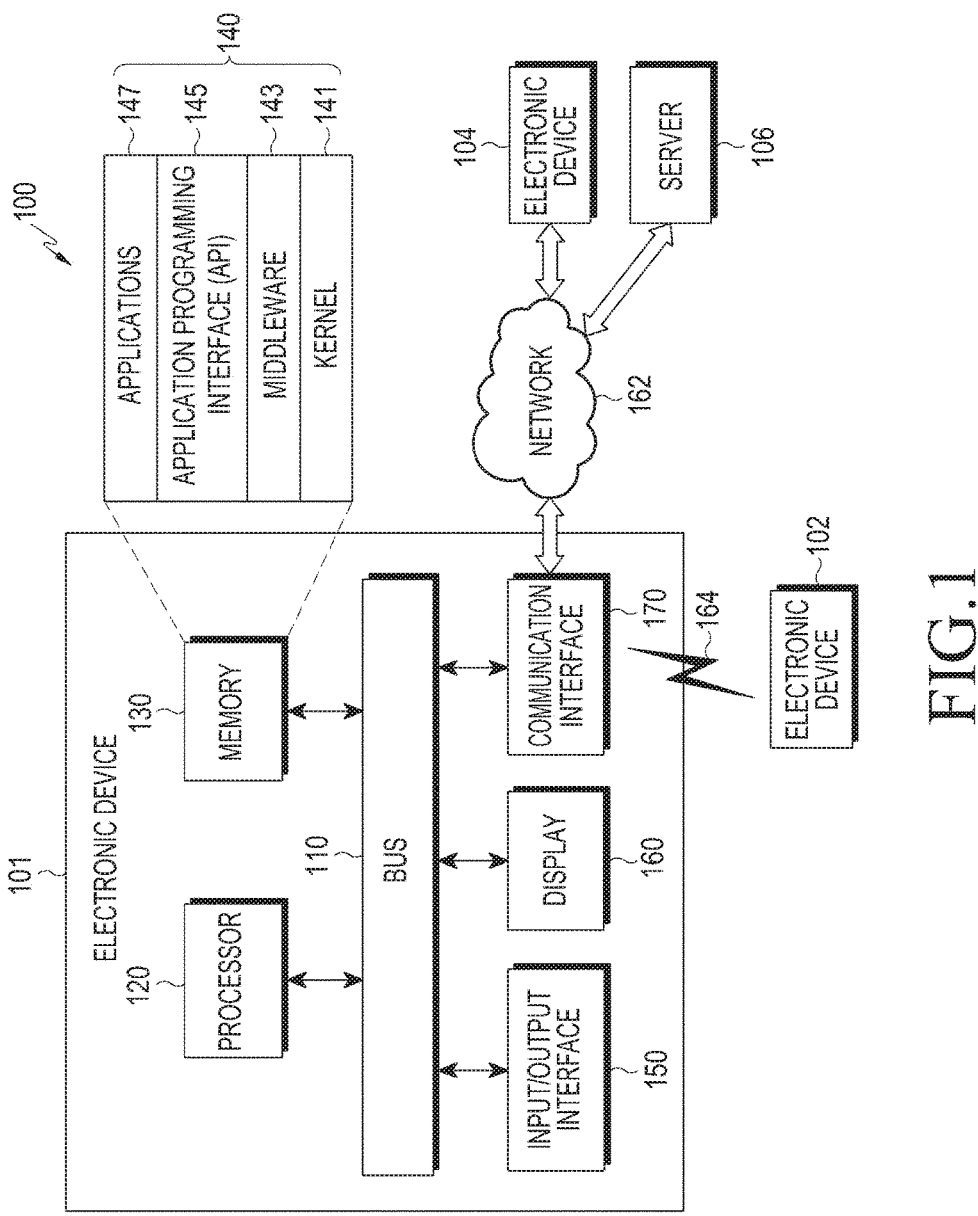
FIG. 1 is a view illustrating an electronic device in a network environment according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

As used herein, the terms "have," "may have," "include," or "may include" a feature (e.g., a number, function, operation, or a component such as a part) indicate the existence of the feature and do not exclude the existence of other features.

As used herein, the terms "A or B," "at least one of A and/or B," or "one or more of A and/or B" may include all possible combinations of A and B. For example, "A or B," "at least one of A and B," "at least one of A or B" may indicate all of (1) including at least one A, (2) including at least one B, or (3) including at least one A and at least one B.

As used herein, the terms "first" and "second" may modify various components regardless of importance and/or order and are used to distinguish a component from another without limiting the components. For example, a first user device and a second user device may indicate different user devices from each other regardless of the order or importance of the devices. For example, a first component may be denoted a second component, and vice versa without departing from the scope of the present disclosure.

It will be understood that when an element (e.g., a first element) is referred to as being (operatively or communicatively) "coupled with/to," or "connected with/to" another element (e.g., a second element), it can be coupled or connected with/to the other element directly or via a third element. In contrast, it will be understood that when an element (e.g., a first element) is referred to as being "directly coupled with/to" or "directly connected with/to" another element (e.g., a second element), no other element (e.g., a third element) intervenes between the element and the other element.

As used herein, the terms "configured (or set) to" may be interchangeably used with the terms "suitable for," "having the capacity to," "designed to," "adapted to," "made to," or "capable of" depending on circumstances. The term "configured (or set) to" does not essentially mean "specifically designed in hardware to." Rather, the term "configured to" may mean that a device can perform an operation together with another device or parts. For example, the term "processor configured (or set) to perform A, B, and C" may mean a generic-purpose processor (e.g., a central processing unit (CPU) or application processor (AP) that may perform the operations by executing one or more software programs stored in a memory device or a dedicated processor (e.g., an embedded processor) for performing the operations.

The terms as used herein are provided merely to describe some embodiments thereof, but not to limit the scope of other embodiments of the present disclosure. The terms including technical and scientific terms used herein have the same meaning as commonly understood by one of ordinary skill in the art to which the embodiments of the present disclosure belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some cases, the terms defined herein may be interpreted to exclude embodiments of the present disclosure.

For example, examples of the electronic device according to embodiments of the present disclosure may include at least one of a smartphone, a tablet personal computer (PC), a mobile phone, a video phone, an e-book reader, a desktop PC, a laptop computer, a netbook computer, a workstation, a server, a personal digital assistant (PDA), a portable multimedia player (PMP), a Moving Picture Experts Group phase 1 or phase 2 (MPEG-1 or MPEG-2) audio layer 3 (MP3) player, a mobile medical device, a camera, or a wearable device. According to an embodiment of the present disclosure, the wearable device may include at least one of an accessory-type device (e.g., a watch, a ring, a bracelet, an anklet, a necklace, glasses, contact lenses, or a head-mounted device (HMD)), a fabric- or clothes-integrated device (e.g., electronic clothes), a body attaching-type device (e.g., a skin pad or tattoo), or a body implantable device (e.g., an implantable circuit).

In some embodiments, the electronic device may be a home appliance. Examples of the home appliance may include at least one of a television, a digital versatile disc (DVD) player, an audio player, a refrigerator, an air conditioner, a cleaner, an oven, a microwave oven, a washer, a drier, an air cleaner, a set-top box, a home automation control panel, a security control panel, a television (TV) box (e.g., Samsung HomeSync™, Apple TV™, or Google TV™), a gaming console (Xbox™, PlayStation™), an electronic dictionary, an electronic key, a camcorder, a charger, or an electronic picture frame.

According to an embodiment of the present disclosure, examples of the electronic device may include at least one of various medical devices (e.g., diverse portable medical measuring devices (a blood sugar measuring device, a heartbeat measuring device, or a body temperature measuring device), a magnetic resource angiography (MRA) device, a magnetic resource imaging (MRI) device, a computed tomography (CT) device, an imaging device, or an ultrasonic device), a navigation device, a global navigation satellite system (GNSS) receiver, an event data recorder (EDR), a flight data recorder (FDR), an automotive infotainment device, an sailing electronic device (e.g., a sailing navigation device or a gyro compass), avionics, security devices, vehicular head units, industrial or home robots, automatic teller's machines (ATMs), point of sales (POS) devices, or internet of things (IoT) devices (e.g., a bulb, various sensors, an electric or gas meter, a sprinkler, a fire alarm, a thermostat, a street light, a toaster, fitness equipment, a hot water tank, a heater, or a boiler).

According to various embodiments of the disclosure, examples of the electronic device may at least one of part of a piece of furniture or building/structure, an electronic board, an electronic signature receiving device, a projector, or various measurement devices (e.g., devices for measuring water, electricity, gas, or electromagnetic waves). According to an embodiment of the present disclosure, the electronic device may be one or a combination of the above-listed devices. According to an embodiment of the present disclosure, the electronic device may be a flexible electronic device. The electronic device disclosed herein is not limited to the above-listed devices, and may include new electronic devices depending on the development of technology.

Hereinafter, electronic devices are described with reference to the accompanying drawings, according to various embodiments of the present disclosure. As used herein, the term "user" may denote a human or another device (e.g., an artificial intelligent electronic device) using the electronic device.

FIG. 1 is a view illustrating an electronic device 101 in a network environment 100 according to an embodiment of the present disclosure.

Referring to FIG. 1, the electronic device 101 may include a bus 110, a processor 120, a memory 130, an input/output interface 150, a display 160, and a communication interface 170. In some embodiments, the electronic device 101 may exclude at least one of the components or may add another component.

The bus 110 may include a circuit for connecting the components 110 to 170 with one another and transferring communications (e.g., control messages and/or data) between the components.

The processor 120 may include one or more of a CPU, an AP, or a communication processor (CP). The processor 120 may perform control on at least one of the other components of the electronic device 101, and/or perform an operation or data processing relating to communication.

The memory 130 may include a volatile and/or non-volatile memory. For example, the memory 130 may store commands or data related to at least one other component of the electronic device 101. According to an embodiment of the present disclosure, the memory 130 may store software and/or a program 140. The program 140 may include, e.g., a kernel 141, middleware 143, an application programming interface (API) 145, and/or an application program (or "application") 147. At least a portion of the kernel 141, middleware 143, or API 145 may be denoted an operating system (OS).

For example, the kernel 141 may control or manage system resources (e.g., the bus 110, processor 120, or a memory 130) used to perform operations or functions implemented in other programs (e.g., the middleware 143, API 145, or application program 147). The kernel 141 may provide an interface that allows the middleware 143, the API 145, or the application 147 to access the individual components of the electronic device 101 to control or manage the system resources.

The middleware 143 may function as a relay to allow the API 145 or the application 147 to communicate data with the kernel 141, for example.

Further, the middleware 143 may process one or more task requests received from the application program 147 in order of priority. For example, the middleware 143 may assign at least one of application programs 147 with priority of using system resources (e.g., the bus 110, processor 120, or memory 130) of the electronic device 101. For example, the middleware 143 may perform scheduling or load balancing on the one or more task requests by processing the one or more task requests according to the priority assigned to the at least one application program 147.

The API 145 is an interface allowing the application 147 to control functions provided from the kernel 141 or the middleware 143. For example, the API 145 may include at least one interface or function (e.g., a command) for filing control, window control, image processing or text control.

The input/output interface 150 may serve as an interface that may, e.g., transfer commands or data input from a user or other external devices to other component(s) of the electronic device 101. Further, the input/output interface 150 may output commands or data received from other component(s) of the electronic device 101 to the user or the other external device.

The display 160 may include, e.g., a liquid crystal display (LCD), a light emitting diode (LED) display, an organic light emitting diode (OLED) display, or a microelectromechanical systems (MEMS) display, or an electronic paper display. The display 160 may display, e.g., various contents (e.g., text, images, videos, icons, or symbols) to the user. The display 160 may include a touchscreen and may receive, e.g., a touch, gesture, proximity or hovering input using an electronic pen or a body portion of the user.

For example, the communication interface 170 may set up communication between the electronic device 101 and an external electronic device (e.g., a first electronic device 102, a second electronic device 104, or a server 106). For example, the communication interface 170 may be connected with the network 162 through wireless or wired communication to communicate with the external electronic device (e.g., the second external electronic device 104 or server 106).

The wireless communication may use at least one of, e.g., long term evolution (LTE), long term evolution-advanced (LTE-A), code division multiple access (CDMA), wideband code division multiple access (WCDMA), universal mobile telecommunication system (UNITS), wireless broadband (WiBro), or global system for mobile communication (GSM), as a cellular communication protocol. Further, the wireless communication may include, e.g., short-range communication 164. The short-range communication 164 may include at least one of, e.g., Wi-Fi, bluetooth (BT), near-field communication (NFC), or global navigation satellite system (GNSS). The GNSS may include at least one of, e.g., global positioning system (GPS), global navigation satellite system (Glonass), Beidou navigation satellite system (hereinafter, "Beidou") or Galileo, or the European global satellite-based navigation system. Hereinafter, the terms "GPS" and the "GNSS" may be interchangeably used herein. The wired connection may include at least one of, e.g., universal serial bus (USB), high definition multimedia interface (HDMI), recommended standard (RS)-232, or plain old telephone service (POTS). The network 162 may include at least one of communication networks, e.g., a computer network (e.g., local area network (LAN) or wide area network (WAN)), Internet, or a telephone network.

The first and second external electronic devices 102 and 104 each may be a device of the same or a different type from the electronic device 101. According to an embodiment of the present disclosure, the server 106 may include a group of one or more servers. According to an embodiment of the present disclosure, all or some of operations executed on the electronic device 101 may be executed on another or multiple other electronic devices (e.g., the electronic devices 102 and 104 or server 106). According to an embodiment of the present disclosure, when the electronic device 101 should perform some function or service automatically or at a request, the electronic device 101, instead of executing the function or service on its own or additionally, may request another device (e.g., electronic devices 102 and 104 or server 106) to perform at least some functions associated therewith. The other electronic device (e.g., electronic devices 102 and 104 or server 106) may execute the requested functions or additional functions and transfer a result of the execution to the electronic device 101. The electronic device 101 may provide a requested function or service by processing the received result as it is or additionally. To that end, a cloud computing, distributed computing, or client-server computing technique may be used, for example.

Figure 2:
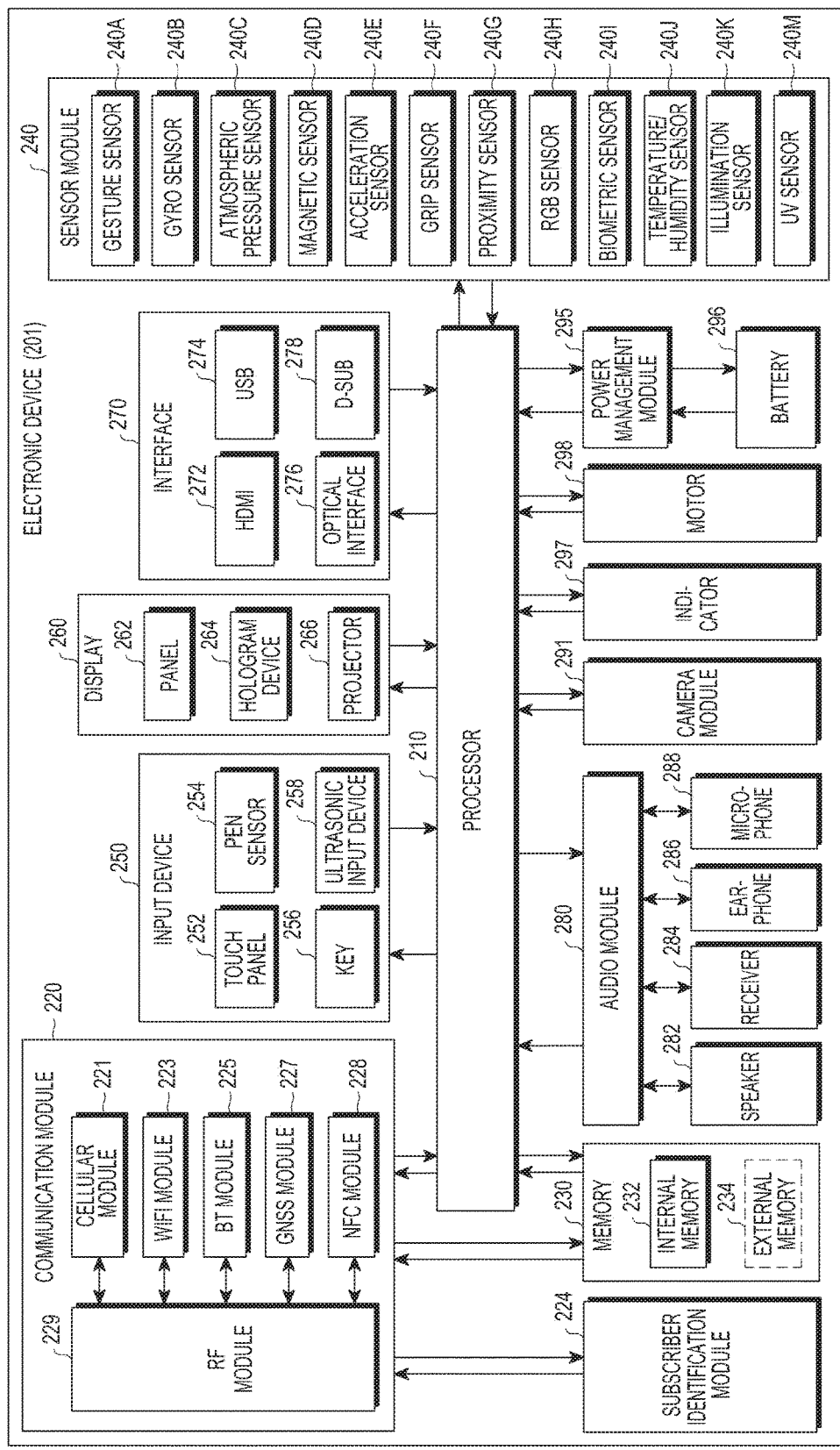
FIG. 2 is a block diagram illustrating an electronic device according to an embodiment of the present disclosure.

FIG. 2 is a block diagram illustrating an electronic device 201 according to an embodiment of the present disclosure.

Referring to FIG. 2, the electronic device 201 may include the whole or part of, e.g., the electronic device 101 shown in FIG. 1. The electronic device 201 may include one or more processors (e.g., APs) 210, a communication module 220, a subscriber identification module (SIM) 224, a memory 230, a sensor module 240, an input device 250, a display 260, an interface 270, an audio module 280, a camera module 291, a power management module 295, a battery 296, an indicator 297, and a motor 298.

The processor 210 may control multiple hardware and software components connected to the processor 210 by running, e.g., an operating system or application programs, and the processor 210 may process and compute various data. The processor 210 may be implemented in, e.g., a system on chip (SoC). According to an embodiment of the present disclosure, the processor 210 may further include a graphic processing unit (GPU) and/or an image signal processor. The processor 210 may include at least some (e.g., the cellular module 221) of the components shown in FIG. 2. The processor 210 may load a command or data received from at least one of other components (e.g., a non-volatile memory) on a volatile memory, process the command or data, and store various data in the non-volatile memory.

The communication module 220 may have the same or similar configuration to the communication interface 170 of FIG. 1. The communication module 220 may include, e.g., a cellular module 221, a Wi-Fi module 223, a BT module 225, a GNSS module 227, a NFC module 228, and a RF module 229.

The cellular module 221 may provide voice call, video call, text, or Internet services through, e.g., a communication network. According to an embodiment of the present disclosure, the cellular module 221 may perform identification or authentication on the electronic device 201 in the communication network using a subscriber identification module 224 (e.g., the SIM card). According to an embodiment of the present disclosure, the cellular module 221 may perform at least some of the functions providable by the processor 210. According to an embodiment of the present disclosure, the cellular module 221 may include a CP.

The Wi-Fi module 223, the BT module 225, the GNSS module 227, or the NFC module 228 may include a process for, e.g., processing data communicated through the module. According to an embodiment of the present disclosure, at least some (e.g., two or more) of the cellular module 221, the Wi-Fi module 223, the Bluetooth module 225, the GNSS module 227, or the NFC module 228 may be included in a single integrated circuit (IC) or an IC package.

The RF module 229 may communicate data, e.g., communication signals (e.g., RF signals). The RF module 229 may include, e.g., a transceiver, a power amp module (PAM), a frequency filter, a low noise amplifier (LNA), or an antenna. According to an embodiment of the present disclosure, at least one of the cellular module 221, the Wi-Fi module 223, the BT module 225, the GNSS module 227, or the NFC module 228 may communicate RF signals through a separate RF module.

The subscription identification module 224 may include, e.g., a card including a subscriber identification module and/or an embedded SIM, and may contain unique identification information (e.g., an integrated circuit card identifier (ICCID) or subscriber information (e.g., an international mobile subscriber identity (IMSI)).

The memory 230 (e.g., the memory 130) may include, e.g., an internal memory 232 or an external memory 234. The internal memory 232 may include at least one of, e.g., a volatile memory (e.g., a dynamic RAM (DRAM), a static RAM (SRAM), a synchronous dynamic RAM (SDRAM), etc.) or a non-volatile memory (e.g., a one-time programmable ROM (OTPROM), a programmable ROM (PROM), an erasable and programmable ROM (EPROM), an electrically erasable and programmable ROM (EEPROM), a mask ROM, a flash ROM, a flash memory (e.g., a NAND flash, or a NOR flash), a hard drive, or solid-state drive (SSD).

The external memory 234 may further include a flash drive, e.g., a compact flash (CF) memory, a secure digital (SD) memory, a micro-SD memory, a min-SD memory, an extreme digital (xD) memory, a multi-media card (MMC), or a memory Stick™. The external memory 234 may be functionally and/or physically connected with the electronic device 201 via various interfaces.

For example, the sensor module 240 may measure a physical quantity or detect a motion state of the electronic device 201, and the sensor module 240 may convert the measured or detected information into an electrical signal. The sensor module 240 may include at least one of, e.g., a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H (e.g., a red-green-blue (RGB) sensor, a bio sensor 240I, a temperature/humidity sensor 240J, an illumination sensor 240K, or an ultra violet (UV) sensor 240M. Additionally or alternatively, the sensor module 240 may include, e.g., an e-nose sensor, an electromyography (EMG) sensor, an electroencephalogram (EEG) sensor, an electrocardiogram (ECG) sensor, an infrared (IR) sensor, an iris sensor, or a finger print sensor. The sensor module 240 may further include a control circuit for controlling at least one or more of the sensors included in the sensing module. According to an embodiment of the present disclosure, the electronic device 201 may further include a processor configured to control the sensor module 240 as part of the processor 210 or separately from the processor 210, and the electronic device 2701 may control the sensor module 240 while the processor 1210 is in a sleep mode.

The input device 250 may include, e.g., a touch panel 252, a (digital) pen sensor 254, a key 256, or an ultrasonic input device 258. The touch panel 252 may use at least one of capacitive, resistive, infrared, or ultrasonic methods. The touch panel 252 may further include a control circuit. The touch panel 252 may further include a tactile layer and may provide a user with a tactile reaction.

The (digital) pen sensor 254 may include, e.g., a part of a touch panel or a separate sheet for recognition. The key 256 may include e.g., a physical button, optical key or key pad. The ultrasonic input device 258 may sense an ultrasonic wave generated from an input tool through a microphone (e.g., the microphone 288) to identify data corresponding to the sensed ultrasonic wave.

The display 260 (e.g., the display 160) may include a panel 262, a hologram device 264, or a projector 266. The panel 262 may have the same or similar configuration to the display 160 of FIG. 1. The panel 262 may be implemented to be flexible, transparent, or wearable. The panel 262 may also be incorporated with the touch panel 252 in a module. The hologram device 264 may make three dimensional (3D) images (holograms) in the air by using light interference. The projector 266 may display an image by projecting light onto a screen. The screen may be, for example, located inside or outside of the electronic device 201. In accordance with an embodiment, the display 260 may further include a control circuit to control the panel 262, the hologram device 264, or the projector 266.

The interface 270 may include e.g., a HDMI 272, a USB 274, an optical interface 276, or a D-subminiature (D-sub) 278. The interface 270 may be included in e.g., the communication interface 170 shown in FIG. 1. Additionally or alternatively, the interface 270 may include a mobile high-definition link (MHL) interface, a SD card/multimedia card (MMC) interface, or infrared data association (IrDA) standard interface.

The audio module 280 may converting, e.g., a sound signal into an electrical signal and vice versa. At least a part of the audio module 280 may be included in e.g., the input/output interface 150 as shown in FIG. 1. The audio module 280 may process sound information input or output through e.g., a speaker 282, a receiver 284, an earphone 286, or a microphone 288.

For example, the camera module 291 may be a device for capturing still images and videos, and may include, according to an embodiment of the present disclosure, one or more image sensors (e.g., front and back sensors), a lens, an image signal processor (ISP), or a flash such as an LED or xenon lamp.

The power management module 295 may manage power of the electronic device 201, for example. The electronic device 201 may be an electronic device powered by a battery, but is not limited thereto. According to an embodiment of the present disclosure, the power management module 295 may include a power management integrated circuit (PMIC), a charger IC, or a battery or fuel gauge. The PMIC may have a wired and/or wireless recharging scheme. The wireless charging scheme may include e.g., a magnetic resonance scheme, a magnetic induction scheme, or an electromagnetic wave based scheme, and an additional circuit, such as a coil loop, a resonance circuit, a rectifier, or the like may be added for wireless charging. The battery gauge may measure an amount of remaining power of the battery 296, a voltage, a current, or a temperature while the battery 296 is being charged. The battery 296 may include, e.g., a rechargeable battery or a solar battery.

The indicator 297 may indicate a particular state of the electronic device 201 or a part (e.g., the processor 210) of the electronic device, including e.g., a booting state, a message state, or recharging state. The motor 298 may convert an electric signal to a mechanical vibration and may generate a vibrational or haptic effect. Although not shown, a processing unit for supporting mobile TV, such as a GPU may be included in the electronic device 201. The processing unit for supporting mobile TV may process media data conforming to a standard for digital multimedia broadcasting (DMB), digital video broadcasting (DVB), or mediaFlo™.

Each of the aforementioned components of the electronic device may include one or more parts, and a name of the part may vary with a type of the electronic device. The electronic device in accordance with various embodiments of the present disclosure may include at least one of the aforementioned components, omit some of them, or include other additional component(s). Some of the components may be combined into an entity, but the entity may perform the same functions as the components may do.

Figure 3:
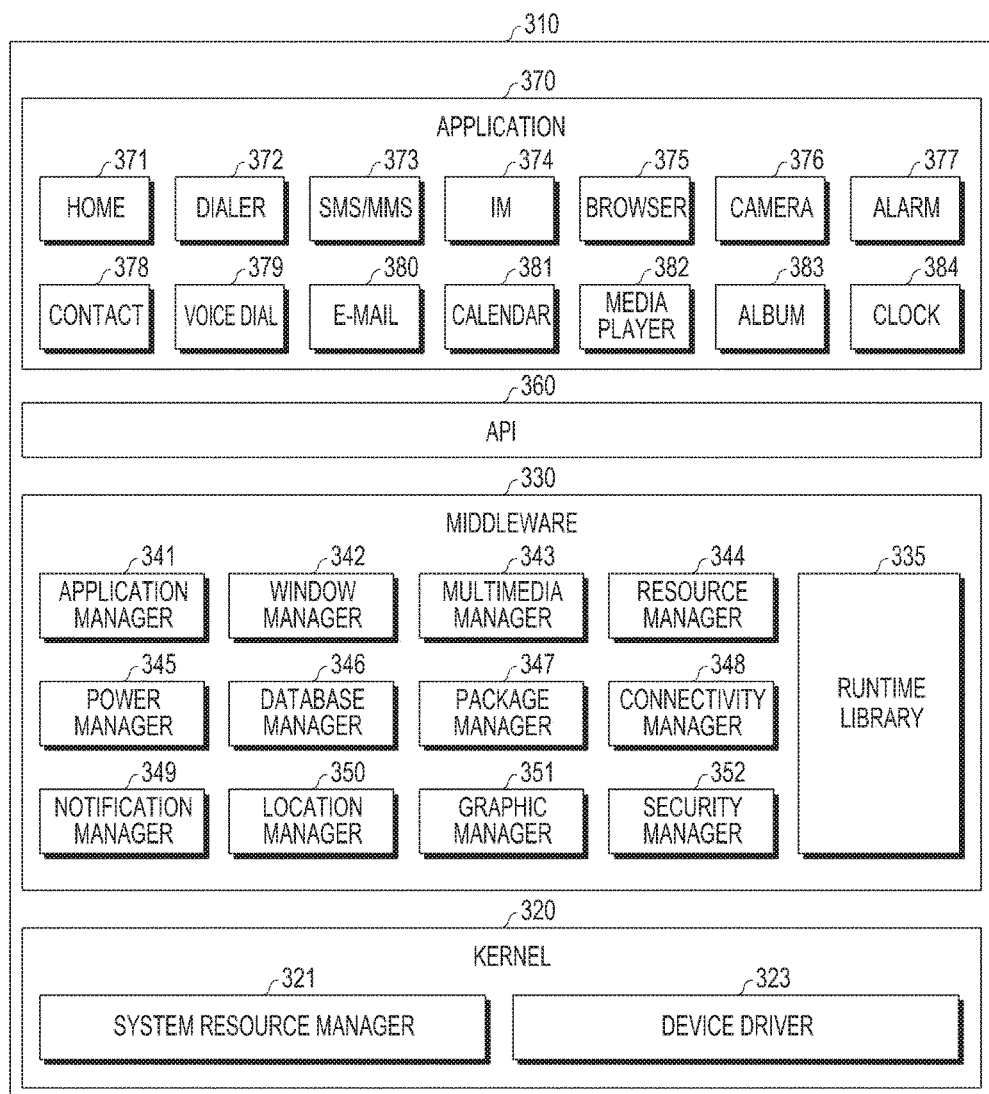
FIG. 3 is a block diagram illustrating a program module according to an embodiment of the present disclosure.

FIG. 3 is a block diagram illustrating a program module according to an embodiment of the present disclosure.

Referring to FIG. 3, the program module 310 (e.g., the program 140) may include an OS controlling resources related to the electronic device (e.g., the electronic device 101) and/or various applications (e.g., the application 147) driven on the operating system. The operating system may include, e.g., Android™, iOS™, Windows™, Symbian™, Tizen™, or Samsung Bada OS™.

The program module 310 may include, e.g., a kernel 320, middleware 330, an API 360, and/or an application 370. At least a part of the program module 310 may be preloaded on the electronic device or may be downloaded from an external electronic device (e.g., the electronic devices 102 and 104 or server 106).

The kernel 320 (e.g., the kernel 141) may include, e.g., a system resource manager 321 and/or a device driver 323. The system resource manager 321 may perform control, allocation, or recovery of system resources. According to an embodiment of the present disclosure, the system resource manager 321 may include a process managing unit, a memory managing unit, or a file system managing unit. The device driver 323 may include, e.g., a display driver, a camera driver, a BT driver, a shared memory driver, a USB driver, a keypad driver, a Wi-Fi driver, an audio driver, or an inter-process communication (IPC) driver.

The middleware 330 may provide various functions to the application 370 through the API 360 so that the application 370 may efficiently use limited system resources in the electronic device or provide functions jointly required by applications 370. According to an embodiment of the present disclosure, the middleware 330 (e.g., the middleware 143) may include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, or a security manager 352.

The runtime library 335 may include a library module used by a compiler in order to add a new function through a programming language while, e.g., the application 370 is being executed. The runtime library 335 may perform input/output management, memory management, or operation on arithmetic functions.

The application manager 341 may manage the life cycle of at least one application of, e.g., the applications 370. The window manager 342 may manage GUI resources used on the screen. The multimedia manager 343 may grasp formats necessary to play various media files and use a codec appropriate for a format to perform encoding or decoding on media files. The resource manager 344 may manage resources, such as source code of at least one of the applications 370, memory or storage space.

The power manager 345 may operate together with, e.g., a basic input/output system (BIOS) to manage battery or power and provide power information necessary for operating the electronic device. The database manager 346 may generate, search, or vary a database to be used in at least one of the applications 370. The package manager 347 may manage installation or update of an application that is distributed in the form of a package file.

The connectivity manager 348 may manage wireless connectivity, such as, e.g., Wi-Fi or BT. The notification manager 349 may display or notify an event, such as a coming message, appointment, or proximity notification, of the user without interfering with the user. The location manager 350 may manage locational information on the electronic device. The graphic manager 351 may manage graphic effects to be offered to the user and their related user interface. The security manager 352 may provide various security functions necessary for system security or user authentication. According to an embodiment of the present disclosure, when the electronic device (e.g., the electronic device 101) has telephony capability, the middleware 330 may further include a telephony manager for managing voice call or video call functions of the electronic device.

The middleware 330 may include a middleware module forming a combination of various functions of the above-described components. The middleware 330 may provide a specified module per type of the operating system in order to provide a differentiated function. Further, the middleware 330 may dynamically omit some existing components or add new components.

The API 360 (e.g., the API 145) may be a set of, e.g., API programming functions and may have different configurations depending on operating systems. For example, in the case of Android or iOS, one API set may be provided per platform, and in the case of Tizen, two or more API sets may be offered per platform.

The application 370 (e.g., the application 147) may include one or more applications that may provide functions such as, e.g., a home 371, a dialer 372, a short message service (SMS)/multimedia messaging service (MMS) 373, an instant message (IM) 374, a browser 375, a camera 376, an alarm 377, a contact 378, a voice dial 379, an email 380, a calendar 381, a media player 382, an album 383, or a clock 384, a health-care (e.g., measuring the degree of workout or blood sugar), or provision of environmental information (e.g., provision of air pressure, moisture, or temperature information).

According to an embodiment of the present disclosure, the application 370 may include an application (hereinafter, "information exchanging application" for convenience) supporting information exchange between the electronic device (e.g., the electronic device 101) and an external electronic device (e.g., the electronic devices 102 and 104). Examples of the information exchange application may include, but is not limited to, a notification relay application for transferring specific information to the external electronic device, or a device management application for managing the external electronic device.

For example, the notification relay application may include a function for relaying notification information generated from other applications of the electronic device (e.g., the SMS/MMS application, email application, health-care application, or environmental information application) to the external electronic device (e.g., the electronic devices 102 and 104). Further, the notification relay application may receive notification information from, e.g., the external electronic device and may provide the received notification information to the user.

The device management application may perform at least some functions of the external electronic device (e.g., the electronic device 102 or 104) communicating with the electronic device (for example, turning on/off the external electronic device (or some components of the external electronic device) or control of brightness (or resolution) of the display), and the device management application may manage (e.g., install, delete, or update) an application operating in the external electronic device or a service (e.g., call service or message service) provided from the external electronic device.

According to an embodiment of the present disclosure, the application 370 may include an application (e.g., a health-care application of a mobile medical device) designated according to an attribute of the external electronic device (e.g., the electronic devices 102 and 104). According to an embodiment of the present disclosure, the application 370 may include an application received from the external electronic device (e.g., the server 106 or electronic devices 102 and 104). According to an embodiment of the present disclosure, the application 370 may include a preloaded application or a third-party application downloadable from a server. The names of the components of the program module 310 according to the shown embodiment may be varied depending on the type of operating system.

According to an embodiment of the present disclosure, at least a part of the program module 310 may be implemented in software, firmware, hardware, or in a combination of two or more thereof. At least a part of the program module 310 may be implemented (e.g., executed) by e.g., a processor (e.g., the processor 210). At least a part of the program module 310 may include e.g., a module, program, routine, set of commands, process, or the like for performing one or more functions.

Figure 4:
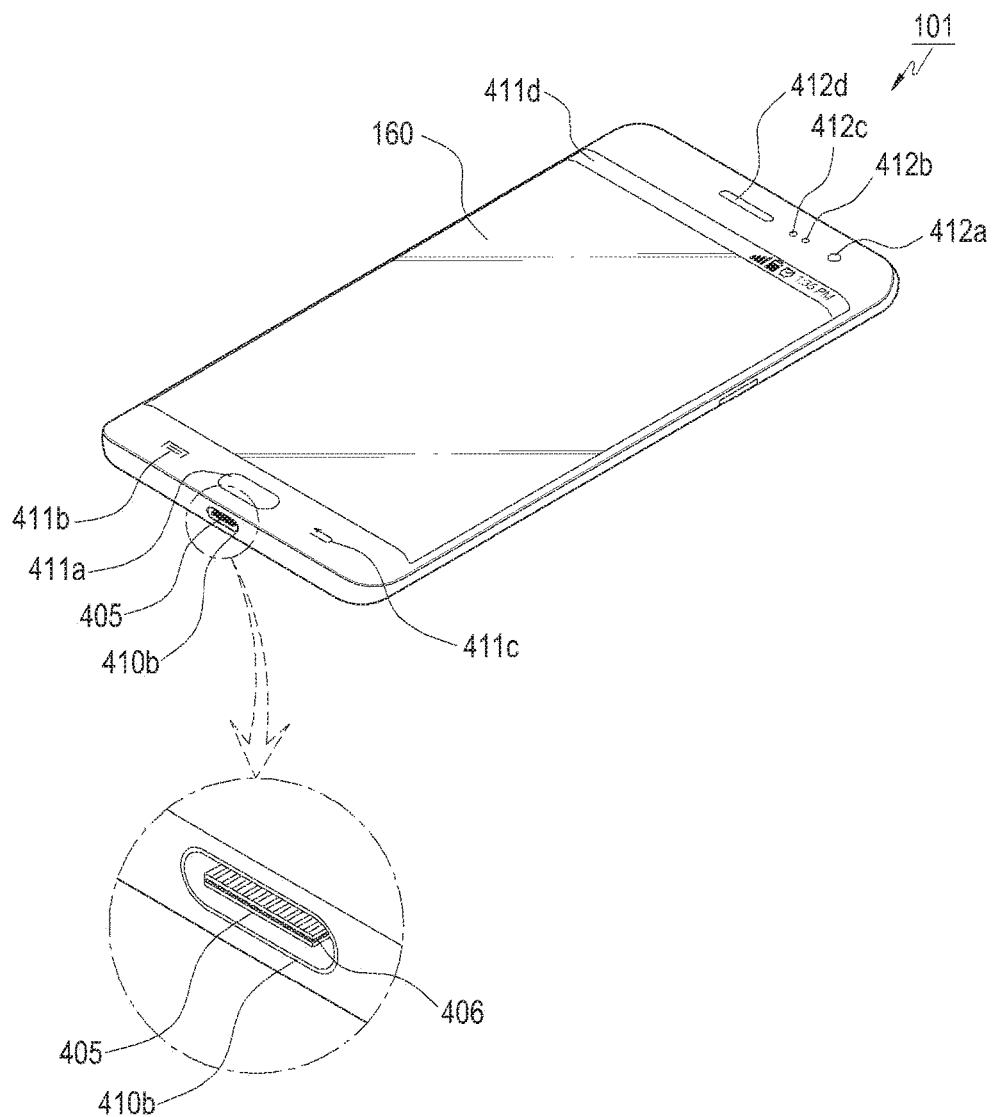
FIG. 4 is a front, perspective view illustrating an electronic device according to an embodiment of the present disclosure.

FIG. 4 is a front, perspective view illustrating an electronic device according to an embodiment of the present disclosure.

Referring to FIG. 4, the electronic device 101 may be a smartphone, wearable device, TV, or tablet PC with a USB type-C connector. A connector 410b of the electronic device 101 may be a receptacle, and a connector of an accessory which may be coupled to the receptacle may be a plug.

Referring to FIG. 4, the display 160 may be disposed in the middle of the front surface of the electronic device 101 to sense touches and hovering. The display 160 may take up most of the front surface of the electronic device 101. FIG. 4 illustrates an example in which a main home screen is displayed on the display 160. The main home screen is a screen that is first to be displayed on the display 160 when the electronic device 101 is powered on. When the electronic device 101 has several pages of different home screens, the main home screen may be the first one of the home screens. The home screen may show up on short-key icons, a main menu shifting key for running applications frequently used, time, and weather. The main menu shifting key may display a menu on the display 160. On the top of the display 160 may be provided a status bar 411d including battery recharge state, signal reception strength, and current time. A home key 411a, a menu button 411b, and a go-back button 411c may be provided on a lower portion of the display 160.

The home key 411a may display the main home screen on the display 160. For example, when the home button 411a is touched while the main home screen and other home screens or menu are in display on the display 160, the main home screen may show up on the display 160. When the home key 411a is touched while applications are running on the display 160, the main home screen may be displayed on the display 160. The home key 411a may be used to display applications recently used or a task manager on the display 160. The menu button 411b may provide a connection menu that may be used on the display 160. The connection menu may include an add widget menu, a change background menu, a search menu, an edit menu, and a setting menu. The go-back button 411c may display the screen displayed immediately before the screen currently in execution or may terminate the latest application used.

According to an embodiment of the present disclosure, a first camera 412a, an illuminance sensor 412b, a proximity sensor 412c, or a speaker 412d may be provided on an upper area of the front surface of the electronic device 101. The electronic device 101 may have a connector 410b for electrical connection with an external electronic device. The connector 410b may be used as an interface for connection between the electronic device 101 and a first external electronic device 102 or a power source (not shown). The electronic device 101 may transmit data stored in a memory 130 of the electronic device 101 to the first external electronic device 102 or receive data from the first external electronic device 102 via a wire cable connected with the connector 410b under the control of the processor 120. The electronic device 101 may receive power from a power source (not shown) or charge a battery (not shown) with the power source through the wire cable connected with the connector 410b. The connector 410b may include a USB type-C connector and may have a contact board 405 inside. A mid plate 406 which is electrically conductive may be formed inside the contact board 405. A plurality of pins may be formed on the top and/or bottom of the contact board 405.

The electronic device 101 may be wiredly connected with the first external electronic device 102 via the connector 410b. In this case, the connector 410b may be shaped or configured to allow for insertion of the plug of the first external electronic device 102 with its top or bottom facing up. As such, the pins of the first external electronic device 102 may be plugged into the connector 410b in either way. The plurality of pins formed on the top and bottom of the contact board 405 may be arranged to be able to transmit or receive data or power regardless of which way the first external electronic device 102 is plugged in.

Figure 5:
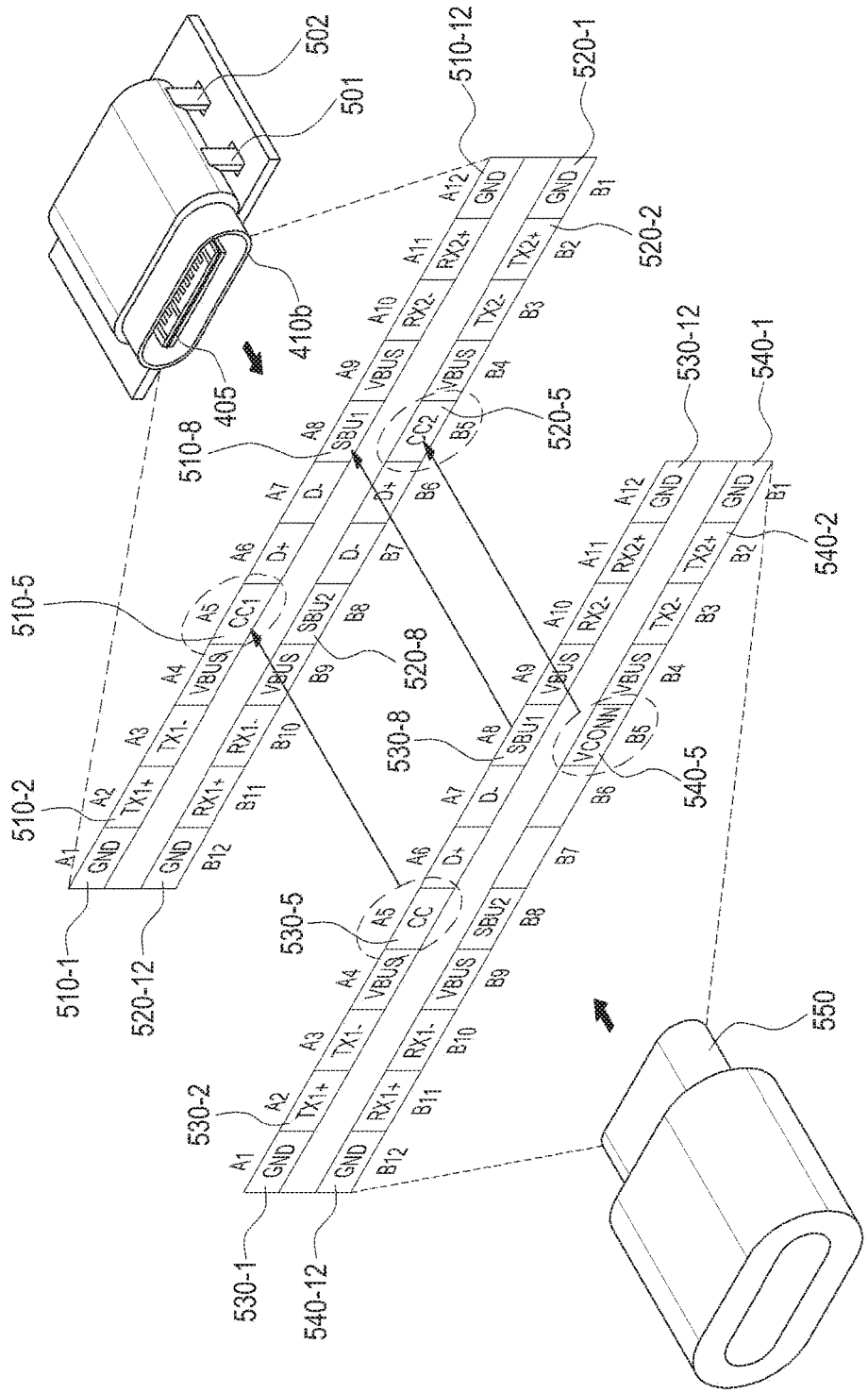
FIG. 5 is a view illustrating examples of functions of a plurality of pins formed on a connector of an electronic device and a connector of an external electronic device according to an embodiment of the present disclosure.

FIG. 5 is a view illustrating examples of functions of a plurality of pins formed on a connector of an electronic device and a connector of an external electronic device according to an embodiment of the present disclosure.

Referring to FIG. 5, the electronic device 101 may be connected with an external electronic device 102 via the connector 410b. The connector 410b of the electronic device 101 may be shaped, formed, or configured to allow the connector 550 of the external electronic device 102 to be plugged therein to with either the top or bottom facing up. The contact board 405 may be formed inside the connector 410b. Twelve pins 510-1, 510-2, . . . , 510-12 and other twelve pins 520-1, 520-2, . . . , 520-12 may be formed on the top and bottom, respectively, of the contact board 405. A mid plate 406 which is electrically conductive may be formed inside the contact board 405. The connector 550 of the external electronic device 102 may have twelve pins 530-1, 530-2, . . . , 530-12 on the top for contacting the twelve pins 510-1, 510-2, . . . , 510-12 formed on the top of the contact board 405 and other twelve pins 540-1, 540-2, . . . , 540-12 on the bottom for contacting the twelve pins 520-1, 520-2, . . . , 520-12 formed on the bottom of the contact board 405. The number of the pins formed in the connector of the external electronic device 102 may be varied depending on the type of the electronic device. Depending on the type, the external electronic device 102 may have one or two configuration channel (CC) pins. For example, the twelve top pins may be the same in order of arrangement as the twelve bottom pins to allow the connector 550 of the external electronic device 102 to be plugged in whichever way. This structure allows the user to plug the cable of the external electronic device 102 into the connector 410b of the electronic device 101 in its flipped position.

The array of the top and bottom pins formed on the contact board 405 is shown in Table 1 below:

TABLE 1

| Pin | Pin | Name | Function | Note |
|---|---|---|---|---|
| A1 | B1 | GND | Power | Support for 60 W minimum (combined with all VBUS pins) |
| A2 | B2 | TX1+ | USB 3.1 or Alternate Mode | 10 Gb/s differential pair with TX1− |
| A3 | B3 | TX1− | USB 3.1 or Alternate Mode | 10 Gb/s differential pair with TX1+ |
| A4 | B4 | VBUS | Power | Support for 60 W minimum (combined with all VBUS pins) |
| A5 | B5 | CC1 | CC or VCONN | — |
| A6 | B6 | D+ | USB 2.0 | — |
| A7 | B7 | D− | USB 2.0 | — |
| A8 | B8 | SBU1 | Alternate Mode | Lower speed side band signal |
| A9 | B9 | VBUS | Power | Support for 60 W minimum (combined with all VBUS pins) |
| A10 | B10 | RX2− | USB 3.1 or Alternate Mode | 10 Gb/s differential pair with RX2 |

TABLE 1-continued

| Pin | Pin | Name | Function | Note |
| --- | --- | --- | --- | --- |
| A11 | B11 | RX2+ | USB 3.1 or Alternate Mode | 10 Gb/s differential pair with RX2− |
| A12 | B12 | GND | Power | Support for 60 W minimum (combined with all VBUS pins) |

The USB type-C connector has 24 pins. The 24 pins may be arranged in a mirrored configuration due to reversibility. This structure allows the user to plug the connector 550 of the external electronic device 102 into the connector 410*b* of the electronic device 101 in its flipped position. In this case, the symmetrical pins might not be used together. For example, when the TX1+ and TX1− pins are in use, the TX2+, TX2−, RX2+, and RX2− pins might not be used, and when the RX1+ and RX1− pins are in use, the RX2+, RX2−, TX2+, and TX2− pins might not. As such, the mid plate 406, which is electrically conductive is provided inside the contact board 405 of the connector 410*b*. Although the contact board 405 has a total of 24 pins (12 on the top and the other 12 on the bottom), corresponding pins might not simultaneously be used. Which pin is to be used may be determined depending on what cable is to be plugged, the connector of the cable, and the state of connection between the connector and the connector 410*b* of the electronic device 101.

The CC1 pin 510-5 formed on the top of the contact board 405 and the CC2 pin 520-5 formed on the bottom of the contact board 405 may be used to figure out the purpose of the external electronic device 102 connected to the connector 410*b*. For example, when the connector 550 of the external electronic device 102 is plugged into the connector 410*b* of the electronic device 101 with its top facing up so that the CC1 pin 510-5 of the electronic device 101 is connected to the CC pin 530-5 of the external electronic device 102, the CC2 pin 520-5 of the electronic device 101 may be used to supply power VCONN for an integrated circuit (IC) for recognizing the external electronic device 102. For example, when the connector 550 of the external electronic device 102 is plugged into the connector 410*b* of the electronic device 101 with its top facing down so that the CC2 pin 520-5 of the electronic device 101 is connected to the CC pin 530-5 of the external electronic device 102, the CC1 pin 510-5 of the electronic device 101 may be used to supply power VCONN for an integrated circuit (IC) for recognizing the external electronic device 102. The CC pins 510-5 and 520-5 of the electronic device 101 may be connected to the CC pin 530-5 or VCONN pin 540-5 of the external electronic device 102, and the CC pins 510-5 and 520-5 of the electronic device 101 may support the CC and VCONN pins.

The SBU1 pin 510-8 and the SBU2 pin 520-8 of the electronic device 101 are low-speed signal pins intended for an alternative mode. Before power transmission or reception, the electronic device 101 and the external electronic device 102 may be required for negotiation of the alternative mode.

Figure 6:
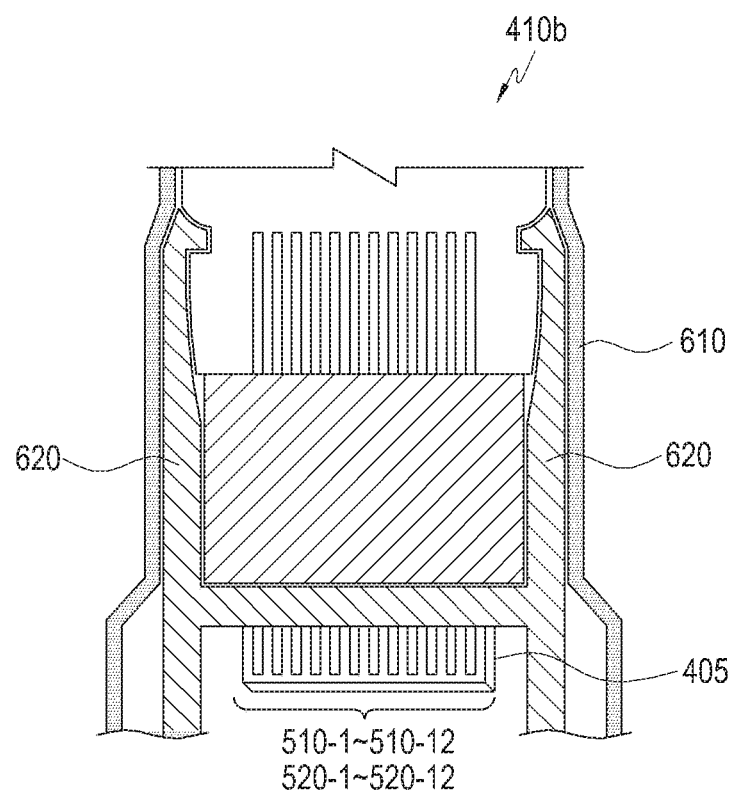
FIG. 6 is a side cross-sectional view illustrating a connector coupled to an external electronic device according to an embodiment of the present disclosure.

FIG. 6 is a side cross-sectional view illustrating a connector coupled to an external electronic device according to an embodiment of the present disclosure.

Referring to FIG. 6, the external electronic device may have two contact pins 620 for electrical connection to the contact board 405 of the connector 410*b* of the electronic device 101. The contact pins 620 may function as a ground. The electronic device 101 may detect connection of the two contact pins 620 of the external electronic device to the contact board 405. The electronic device 101 may apply power to the mid plate 406 formed inside the contact board 405. The electronic device 101 may detect a voltage drop corresponding to connection between the contact pins 620 of the external electronic device and the mid plate 406 formed inside the contact board 405 while applying power to the mid plate 406 formed inside the contact board 405. As such, when the voltage applied to the mid plate 406 of the contact board 405 drops, the electronic device 101 may determine that an external electronic device is connected to the connector 410*b*. An outer metallic part (e.g., a shell part 610) may be attached to the housing of the electronic device 101 to wrap and protect the connector 410*b*. The outer metallic part may serve as a ground. Twelve pins 510-1 to 510-12 and other twelve pins 520-1 to 520-12 are formed on the top and bottom, respectively, of the contact board 405. Each pin formed on the contact board 405 may electrically be connected to a respective one of the pins of the external electronic device, corresponding to the external electronic device being plugged.

Figure 7A:
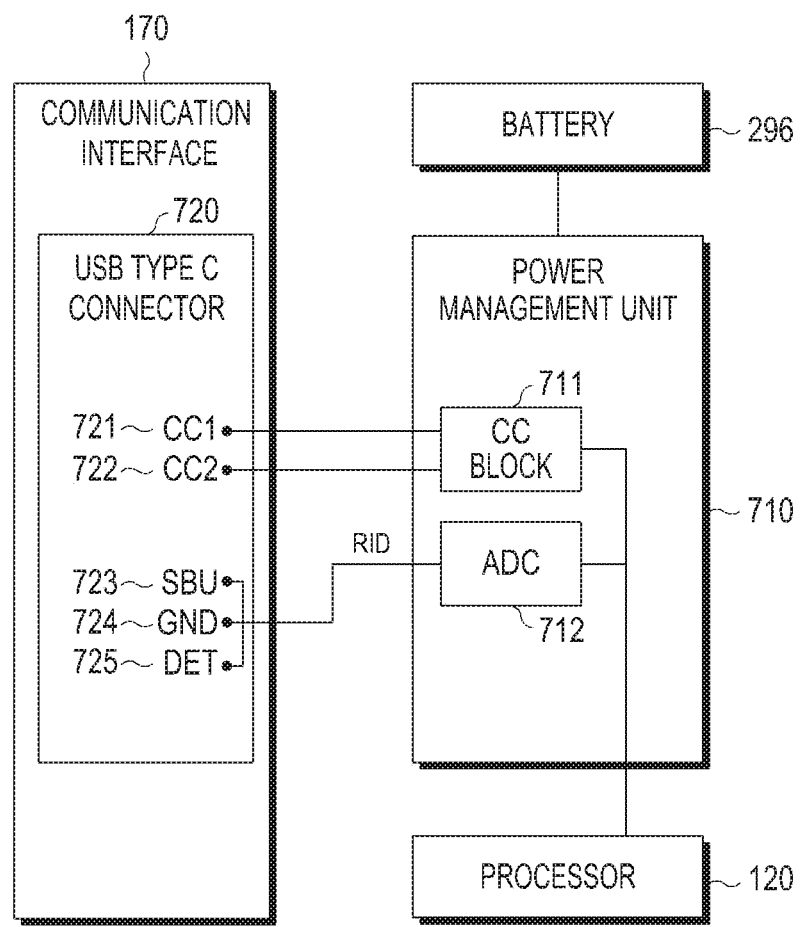
FIG. 7A is a block diagram illustrating an electronic device for preventing corrosion according to an embodiment of the present disclosure.

FIG. 7A is a block diagram illustrating an electronic device for preventing corrosion according to an embodiment of the present disclosure.

Figure 7B:
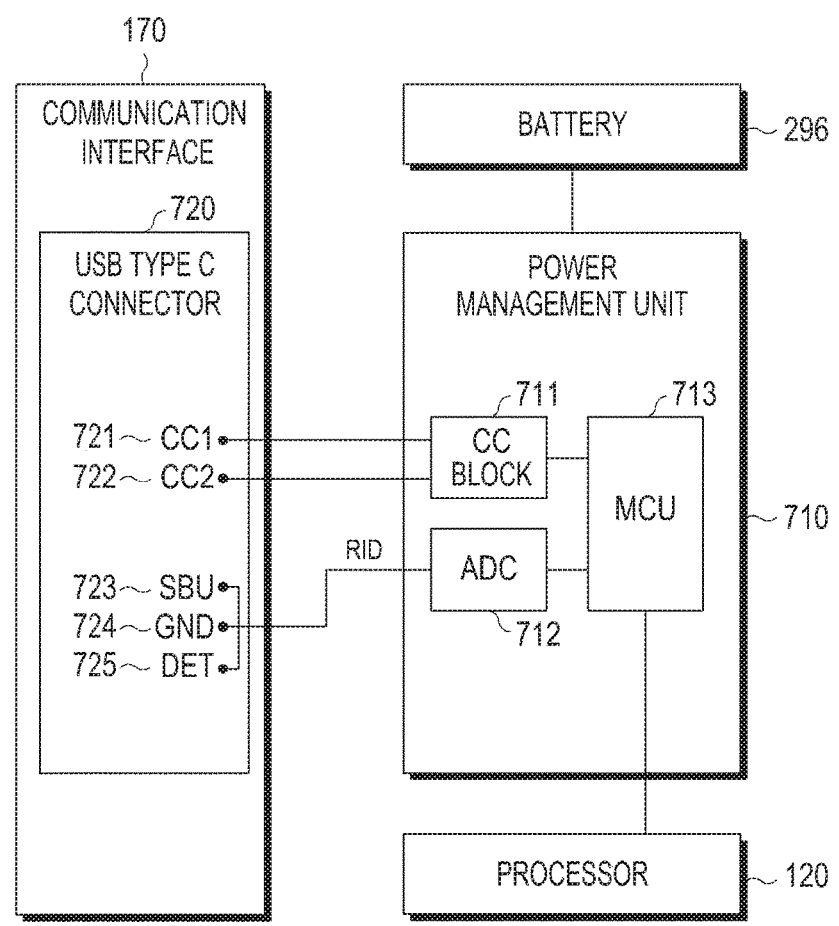
FIG. 7B is a block diagram illustrating an electronic device for preventing corrosion according to an embodiment of the present disclosure.

FIG. 7B is a block diagram illustrating an electronic device for preventing corrosion according to an embodiment of the present disclosure.

Referring to FIGS. 7A and 7B, an electronic device 101 may include a communication interface 170, a battery 296, a power management unit 710, and a processor 120.

According to an embodiment of the present disclosure, the power management unit 710 (e.g., the power management module 295) may manage the power of the electronic device 101. According to an embodiment of the present disclosure, the power management unit 710 may include a PMIC, a charger IC, or a fuel gauge. The PMIC may have a wired and/or wireless recharging scheme. The wireless charging scheme may include e.g., a magnetic resonance scheme, a magnetic induction scheme, or an electromagnetic wave based scheme, and an additional circuit, such as a coil loop, a resonance circuit, a rectifier, or the like may be added for wireless charging. The battery gauge may measure an amount of remaining power of the battery 296, a voltage, a current, or a temperature while the battery 296 is being charged. The battery 296 may include, e.g., a rechargeable battery or a solar battery. The power management unit 710 may supply power to the battery 296 of the electronic device 101 under the control of the processor 120. The power management unit 710 may supply power received from an external power source (not shown) to the electronic device 101 through the communication interface 170. The power management unit 710 may also supply power wirelessly received from an external power source through a wireless charging scheme to the electronic device 101. The power management unit 710 may include a configuration channel (CC) block 711 connected with CC pins of a USB type-C connector and an analog-to-digital (ADC) converter 712 connected with a secondary bus (SBU) pin 723, detection (DET) pin 725, and ground (GND) pin 724 of the USB type-C connector. The power management unit 710 may also include a micro controller unit (MCU). The MCU 713 may perform at least one operation that is executed on the processor 120. The processor 120 may perform at least one operation that is executed on the MCU 713.

According to an embodiment of the present disclosure, the communication interface 170 may perform at least one function or operation that is executed on the communication interface 170 of FIG. 1. The communication interface 170 may include a USB type-C connector 720. The USB type-C connector 720 may have a contact board 405. The contact board 405 may have 12 pins on the top and 12 pins on the bottom. As such, the USB type-C connector may have 24 pins. The 24 pins may be arranged in a mirrored configuration due to reversibility. This structure allows the user to plug the connector 550 of the external electronic device 102 into the connector 410b of the electronic device 101 in its flipped position. In this case, the symmetrical pins might not be used together. The CC1 pin 721 and the CC2 pin 722 included in the USB type-C connector 720 may be connected to the CC block 711 of the power management unit 710. At least one of the SBU pin 723, the GND pin 724, and the DET pin 725 of the USB type-C connector 720 may be connected to the ADC 712 of the power management unit 710. The DET pin 725 may be two contact pins 620 for electrical connection to the contact board 405 of the USB type-C connector 720. The contact pins 620 may function as a ground. The processor 120 may detect connection of the contact pins 620 to the connector. The CC block 711 and ADC 712 of the power management unit 710 may be controlled by the MCU 713 or the processor 120. The MCU 713 may be included, or not, in the power management unit 710. For example, where the MCU 713 is included in the power management unit 710, the MCU 713 may perform at least one operation that the processor 120 of FIG. 7A does. For example, unless the MCU 713 is included in the power management unit 710, the processor 120 of FIG. 7B may perform at least one operation that the MCU 713 does.

According to an embodiment of the present disclosure, the processor 120 (or the MCU 713) may apply a first current to a designated pin of the connector. The processor 120 (or the MCU 713) may apply the first current in a first mode (e.g., a sleep mode or idle mode). The processor 120 (or the MCU 713) may apply the first current to determine whether the external electronic device 102 is connected to the connector (e.g., a USB type-C connector). The processor 120 (or the MCU 713) may apply the first current through a first pin (e.g., CC pin 721 or 722) of the USB type-C connector, determining whether the external electronic device 102 is connected to the connector. According to an embodiment of the present disclosure, the first current may have a designated value (e.g., about 100 µA). The processor 120 (or the MCU 713) may determine whether an interrupt occurs through at least one second pin (e.g., the SBU pin 723, GND pin 724, and the DET pin 725) of the USB type-C connector. For example, the processor 120 (or the MCU 713) may measure a resistance based on a current applied through at least one second pin (e.g., the SBU pin 723, GND pin 724, and the DET pin 725) of the USB type-C connector, and the processor 120 (or the MCU 713) may determine the occurrence of an interrupt based on the measured resistance.

According to an embodiment of the present disclosure, the processor 120 (or the MCU 713) may convert an analog current value applied to the ADC 712 into a digital current value, determining whether an interrupt occurs. For example, where a foreign body (e.g., liquid or fresh water) is introduced into the USB type-C connector, the current applied to the ADC 712 may be varied as compared with when no foreign body is there. In this case, the processor 120 (or the MCU 713) may measure the resistance based on the varied current. When the measured resistance makes a difference from the one when no foreign body gets inside the USB type-C connector, the processor 120 (or the MCU 713) may determine that a foreign body has been introduced into the USB type-C connector. The processor 120 (or the MCU 713) may determine the type of a liquid introduced into the USB type-C connector based on the magnitude of the measured resistance. The processor 120 (or the MCU 713) may determine whether the interrupt has been caused by connection with an external electronic device. According to an embodiment of the present disclosure, the processor 120 (or the MCU 713) may determine connection with the external electronic device based on a signal received from the external electronic device 102. For example, upon connecting with the external electronic device 102 via the USB type-C connector, the processor 120 (or the MCU 713) may perform bi-phase mark coding (BMC) communication. The processor 120 (or the MCU 713) may convert an analog current value applied to the ADC 712 into a digital current value, determining that the external electronic device is connected via the USB type-C connector.

According to an embodiment of the present disclosure, the processor 120 (or the MCU 713) may apply current to the external electronic device connected via the connector. When the electronic device 101 and the external electronic device 102 are physically connected together, the processor 120 (or the MCU 713) may apply a predetermined current to the external electronic device 102 via the USB type-C connector to send a request for information about the external electronic device 102. The predetermined current may be varied depending on the type or specifications of the external electronic device 102. For example, the predetermined current may be larger than the first current (e.g., 100 µA). When the electronic device 101 and the external electronic device 102 are physically connected together, the external electronic device 102 may send information about the external electronic device 102 to the electronic device 101 through the USB type-C connector. The processor 120 (or the MCU 713) may detect liquid. According to an embodiment of the present disclosure, the electronic device 101 may determine whether an interrupt is caused by the inflow of liquid into the USB type-C connector. The processor 120 (or the MCU 713) may determine whether the interrupt caused stems from connection with an external electronic device or the inflow of liquid. The processor 120 (or the MCU 713) may output a result of the inflow of liquid in a popup (not shown) on the display 160, in a voice through the speaker 282, or output as a vibration.

According to an embodiment of the present disclosure, the processor 120 (or the MCU 713) may determine whether liquid (e.g., water, fresh water, etc.) is introduced by applying the first current through a designated pin of the connector. Upon detecting the liquid, the processor 120 (or the MCU 713) may remain or switch to a low-power mode where a current smaller than the first current is applied, preventing corrosion to the connector. The low-power mode may include a mode in which the first current is applied to a designated pin (e.g., a CC pin of the USB type-C connector) of the connector. Upon detecting the liquid, the processor 120 (or the MCU 713) may apply a second current to the CC pin of the USB type-C connector. Upon detecting the liquid, the processor 120 (or the MCU 713) may apply the second current to the designated pin (e.g., the CC pin of the USB type-C connector) of the connector. The second current may have a value from about 0 µA to 1 µA. The electronic device 101 may apply the first current through a first pin (e.g., CC pin 721 or 722) of the USB type-C connector, determining whether the external electronic device 102 is connected to the connector. The processor 120 (or the MCU 713) may determine whether the liquid is in an evaporated state. The electronic device 101 may measure a resistance based on a current applied through at least one second pin (e.g., the SBU pin 723, GND pin 724, and the DET pin 725)

of the USB type-C connector, and the processor 120 (or the MCU 713) may determine whether the liquid is in an activated state based on the measured resistance. The processor 120 (or the MCU 713) may convert an analog current value applied to the ADC 712 into a digital current value, determining whether the liquid is in the evaporated state. For example, when the liquid is determined to be in the evaporated state, the processor 120 (or the MCU 713) may apply the first current.

According to an embodiment of the present disclosure, the processor 120 (or the MCU 713) may detect a designated substance contacting at least one pin of the connector. The processor 120 (or the MCU 713) may detect the inflow of the designated substance (e.g., liquid) into at least one pin of the USB type-C connector. The processor 120 (or the MCU 713) may detect whether at least part of the designated substance contains a substance different from the designated substance through the at least one pin. For example, the processor 120 (or the MCU 713) may determine whether the liquid detected through the at least one pin contains salt or sugar through a variation in the current or voltage passing through the at least one pin. The processor 120 (or the MCU 713) may include a detecting circuit that may detect whether at least part of the designated substance contains a substance different from the designated substance. When the substance detected through the detecting circuit is the designated substance (e.g., salt-free or sugar-free water), the processor 120 (or the MCU 713) may provide first information through the display. The first information may include information indicating that the designated substance has been introduced into the connector. Upon determining that the substance detected through the detecting circuit includes a different substance (e.g., salt or sugar), the processor 120 (or the MCU 713) may provide second information through the display. The second information may include information indicating that the designated substance has been introduced into the connector and that the designated substance contains a different substance (e.g., salt or sugar). The processor 120 (or the MCU 713) may determine, through the detecting circuit, various substances that may be contained in the liquid to change the characteristics of the liquid, as well as sugar or salt.

According to an embodiment of the present disclosure, the processor 120 (or the MCU 713) may measure a resistance based on a current applied through at least one pin included in the connector. When the measured resistance falls within a first range, the processor 120 (or the MCU 713) may determine that the detected substance is the designated substance. The processor 120 (or the MCU 713) may determine the type or concentration of the sensed substance according to the measured resistance. When the measured resistance falls within a second range, the processor 120 (or the MCU 713) may determine that the detected substance contains a different substance. The connector may include at least one other pin through which power is supplied. Upon detecting the designated substance or the different substance-containing substance through the detecting circuit, the processor 120 (or the MCU 713) may cut off the current to the at least one other pin.

According to an embodiment of the present disclosure, the processor 120 (or the MCU 713) may detect a substance introduced into the connector. The processor 120 (or the MCU 713) may determine whether fresh water or sea water is introduced into the connector for a predetermined time. For example, the electronic device 101 may be dropped and immersed in a pool, beach, or other places. The processor 120 (or the MCU 713) may determine whether the place where the electronic device has been immersed is a pool or beach by detecting the type or concentration of the substance introduced into the connector. For example, upon determining that the electronic device 101 has been immersed in a pool, the processor 120 (or the MCU 713) may switch the camera module 291 of the electronic device 101 into a mode where underwater photography is possible or change the user interface of the display 160 to provide underwater photography. For example, the electronic device 101 may determine that the current location is near a pool based on Wi-Fi information around. When the electronic device 101 is immersed in a pool, the processor 120 (or the MCU 713) may switch the camera module 291 of the electronic device 101 into a mode where underwater photography is possible or change the user interface of the display 160 to provide underwater photography. For example, upon determining that the electronic device 101 has been immersed in fresh water, such as in a pool, for a predetermined time, the processor 120 (or the MCU 713) may generate a predetermined signal (e.g., an alert signal, such as distress or emergency signal), using at least one of information about a base station, information about the electronic device 101, and a satellite signal, and transmit the generated signal to a designated external electronic device (e.g., a base station, another user's electronic device, a server of a rescue center, or a server of a hospital). The predetermined signal may contain content that differs corresponding to the external electronic device that receives the signal.

According to an embodiment of the present disclosure, an electronic device may comprise a connector including a first pin and a second pin, a communication interface connected with the connector, and at least one processor electrically connected with the communication interface, wherein the processor may be configured to apply a first current to the first pin, determine whether liquid is introduced into the connector using the second pin, and when the liquid is introduced into the connector, apply a second current smaller than the first current to the first pin.

According to an embodiment of the present disclosure, the processor may convert a value of an analog current passing through the second pin into a digital current value to determine whether the liquid introduced into the connector is evaporated, and when the liquid is evaporated, the process may apply the first current to the first pin.

According to an embodiment of the present disclosure, upon determining that the liquid is not evaporated, the processor may maintain the application of the second current to the first pin.

According to an embodiment of the present disclosure, the processor may determine whether an interrupt occurs due to connection with an external electronic device via the connector, and upon determining that the connection with the external electronic device is made, the processor may apply the first current to the first pin.

According to an embodiment of the present disclosure, the processor may measure a resistance based on a current applied through the second pin and determine that the interrupt occurs based on, at least, the measured resistance.

According to an embodiment of the present disclosure, the processor may be configured to, when the measured resistance falls within a first range, determine that the liquid is a first liquid, and when the measured resistance falls within a second range, determine that the liquid is a second liquid.

According to an embodiment of the present disclosure, the first pin may be a CC pin, and the second pin may include at least one of a SBU pin, a GND pin, and a DET pin.

The CC pin, the SBU pin, and the GND pin may be universal serial bus (USB) type-C pins, and the DET pin may be a pin for detecting insertion of the external electronic device.

According to an embodiment of the present disclosure, the electronic device may further comprise a display. Upon determining that the liquid is introduced, the processor may provide information related to the introduction of the liquid through the display.

According to an embodiment of the present disclosure, the electronic device may further comprise a camera module. The processor may determine that the electronic device has been immersed in the liquid when the determined liquid is present inside the connector for a predetermined time, when the liquid is fresh water, the processor may switch the camera module into an underwater photography mode and changes the display of the electronic device to provide underwater photography, and when the liquid is sea water, the processor may obtain geographical information about the electronic device, generate a signal including the obtained geographical signal, and transmit the signal to an external electronic device.

According to an embodiment of the present disclosure, an electronic device may comprise a connector for connecting with an external electronic device, the connector including at least one pin capable of detecting a contact of a designated substance and a detecting circuit capable of detecting whether at least part of the designated substance contains a substance different from the designated substance through the at least one pin.

According to an embodiment of the present disclosure, the electronic device may further comprise a display and a processor. The processor may be configured to provide first information through the display when a substance detected through the detecting circuit is the designated substance and provide second information through the display when the substance detected through the detecting circuit contains the different substance.

According to an embodiment of the present disclosure, the detecting circuit in the electronic device may measure a resistance based on a current applied through the at least one pin. The processor may be configured to determine that the detected substance is the designated substance when the measured resistance falls within a first range and determine that the detected substance is the substance containing the different substance when the measured resistance falls within a second range.

According to an embodiment of the present disclosure, the connector of the electronic device may include at least one other pin through which power is supplied. The processor may be configured to cut off a current to the at least one other pin upon detecting the designated substance or the substance containing the different substance through the detecting circuit.

Figure 8:
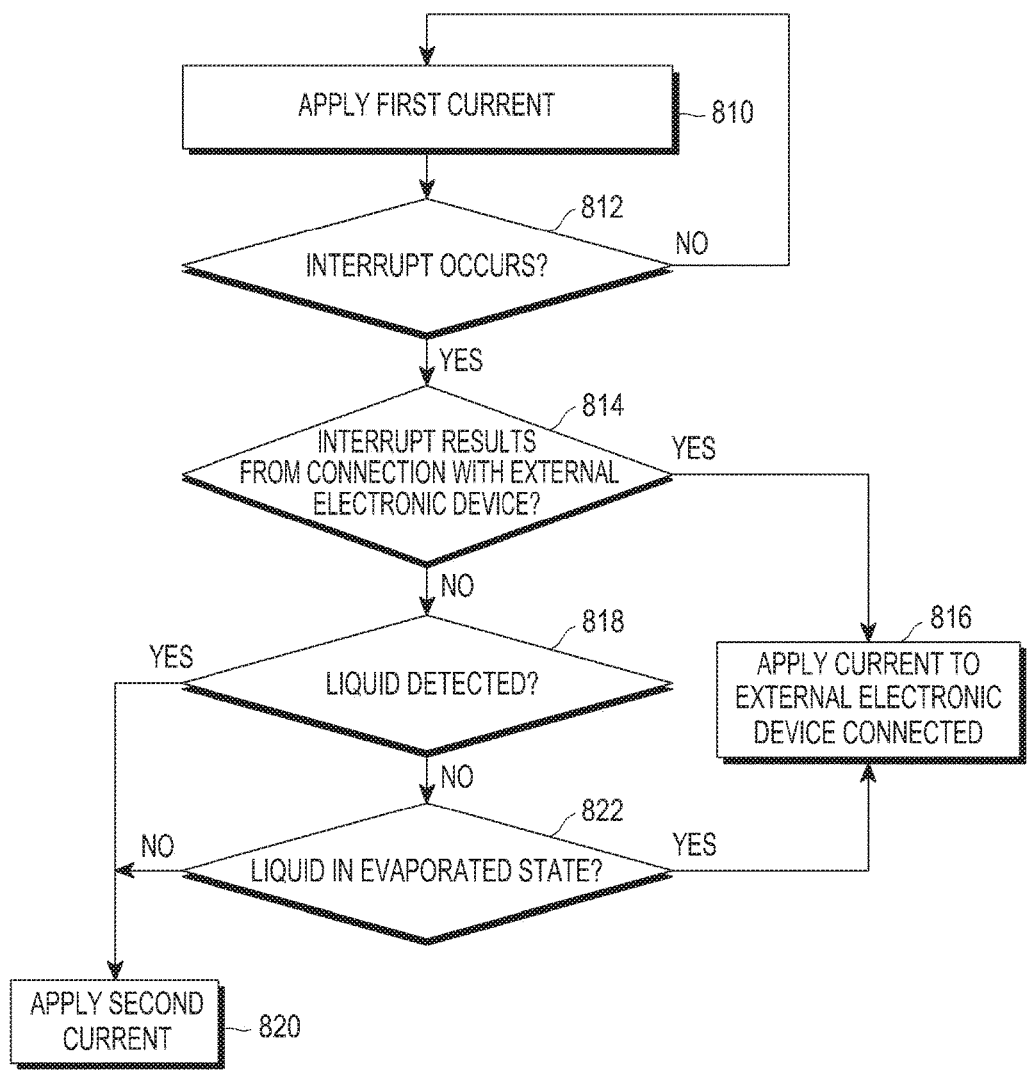
FIG. 8 is a flowchart illustrating operations for preventing corrosion in an electronic device according to an embodiment of the present disclosure.

FIG. 8 is a flowchart illustrating operations for preventing corrosion in an electronic device according to an embodiment of the present disclosure.

Referring to FIG. 8, in operation 810 the electronic device 101 (the processor 120 or the MCU 713) may apply a first current. The electronic device 101 may apply the first current to determine whether an external electronic device 102 is connected to a USB type-C connector. The electronic device 101 may apply the first current through a first pin (e.g., CC pin 721 or 722) of the USB type-C connector, determining whether the external electronic device 102 is connected to the connector. For example, the current may be about 100 μA.

In operation 812, the electronic device 101 (the processor 120 or the MCU 713) may determine whether an interrupt occurs. The electronic device 101 may determine whether an interrupt occurs by detecting a variation in the state of at least one second pin (e.g., the SBU pin 723, GND pin 724, and the DET pin 725) of the USB type-C connector. The variation in state may include a variation in the magnitude of the current or voltage passing through the second pin or a variation in resistance. For example, the electronic device 101 may measure a resistance based on a current applied through at least one second pin (e.g., the SBU pin 723, GND pin 724, and the DET pin 725) of the USB type-C connector, and the electronic device 101 may determine the occurrence of an interrupt based on the measured resistance. For example, the electronic device 101 may measure a resistance based on a voltage applied to the at least one second pin (e.g., the SBU pin 723, GND pin 724, and the DET pin 725) of the USB type-C connector, and the electronic device 101 may determine the occurrence of an interrupt based on the measured resistance. The electronic device 101 may convert an analog current value applied to the ADC 712 into a digital current value, determining whether an interrupt occurs. For example, where a foreign body (e.g., liquid) is introduced into the USB type-C connector, the current applied to the ADC 712 may be varied as compared with when no foreign body is there. In this case, the electronic device 101 may measure the resistance based on the varied current. When the measured resistance makes a difference from the one when no foreign body gets inside the USB type-C connector, the electronic device 101 may determine that a foreign body has been introduced into the USB type-C connector. The electronic device 101 may determine the type of a liquid introduced into the USB type-C connector based on the magnitude of the measured resistance. The memory 130 of the electronic device 101 may store a table representing the type of the foreign body according to each difference in resistance. For example, where the foreign body is sea water, the resistance may be 20KΩ to 200KΩ, and where the foreign body is fresh water, the resistance may be from 200KΩ to 1000KΩ. For example, the electronic device 101 may determine the type of the introduced liquid according to the measured resistance.

In operation 814, the electronic device 101 (the processor 120 or the MCU 713) may determine whether the interrupt caused is attributed to connection with an external electronic device. The electronic device 101 may determine connection with the external electronic device based on a signal received from the external electronic device 102. Upon connecting with the external electronic device 102 via the USB type-C connector, the electronic device 101 may perform bi-phase mark coding (BMC) communication. The electronic device 101 may convert an analog current value applied to the ADC 712 into a digital current value, determining that the external electronic device is connected via the USB type-C connector.

In operation 816, the electronic device 101 (the processor 120 or the MCU 713) may apply current to the external electronic device connected. Upon connecting with the external electronic device 102 via the USB type-C connector, the electronic device 101 may perform bi-phase mark coding (BMC) communication. The electronic device 101 may determine the type of the connected external electronic device 102 through BMC communication. The electronic device 101 and the external electronic device 102 may perform BMC communication by applying a second current while connected together via the USB type-C connector. When the electronic device 101 and the external electronic device 102 are physically connected together, the electronic device 101 may apply a predetermined current to the external electronic device 102 via the USB type-C connector to send a request for information about the external electronic device 102. Alternatively, when the electronic device 101 and the external electronic device 102 are physically connected together, the external electronic device 102 may send information about the external electronic device 102 to the electronic device 101 through the USB type-C connector. The predetermined current may be smaller than the first current. For example, the first current may be about 100 µA, and the second current may be smaller than 100 µA. The second current may be adjusted depending on, e.g., the type or specifications of the external electronic device.

In operation 818, the electronic device 101 (the processor 120 or the MCU 713) may detect liquid. The electronic device 101 may determine whether an interrupt is caused by the inflow of liquid into the USB type-C connector. The electronic device 101 may determine whether the interrupt caused stems from connection with an external electronic device or the inflow of liquid. The electronic device 101 may determine that liquid has been introduced into the USB type-C connector based on the measured resistance. The electronic device 101 may determine the type of a liquid introduced into the USB type-C connector based on the magnitude of the measured resistance. For example, where the foreign body is sea water, the resistance may be 20KΩ to 200KΩ, and where the foreign body is fresh water, the resistance may be from 200KΩ to 1000KΩ. For example, the electronic device 101 may determine the type of the introduced liquid according to the measured resistance. Upon determining that liquid has been introduced, the electronic device 101 may output a result of the introduction to the user. The electronic device 101 may output a result of the inflow of liquid in a popup (not shown) on the display 160, in a voice through the speaker 282, or output as a vibration. Although such a description has been made that operation 818, i.e., detecting liquid, is performed after operation 814, i.e., detecting connection with the external electronic device, this is merely an example. According to an embodiment of the present disclosure, operation 818 may also be performed before operation 814.

In operation 820, the electronic device 101 (the processor 120 or the MCU 713) may apply a second current. Upon detecting liquid, the electronic device 101 may apply the second current to a CC pin of the USB type-C connector. The electronic device 101 may apply the second current via the CC pin of the USB type-C connector, preventing corrosion to the connector. For example, upon detecting liquid, the electronic device 101 may apply the second current that is smaller than the first current to a predesignated pin (e.g., a CC pin of the USB type-C connector) of the connector. The electronic device 101 may apply the second current through a first pin (e.g., a CC pin 721 or 722) of the USB type-C connector, preventing corrosion to at least one pin of the connector.

In operation 822, the electronic device 101 (the processor 120 or the MCU 713) may determine whether the liquid is in an evaporated state. The electronic device 101 may measure a resistance based on a current applied through at least one second pin (e.g., the SBU pin 723, GND pin 724, and the DET pin 725) of the USB type-C connector, and the processor 120 (or the MCU 713) may determine whether the liquid is in an activated state based on the measured resistance. The electronic device 101 may convert an analog current value applied to the ADC 712 into a digital current value, determining whether the liquid is in the evaporated state. For example, when the liquid is determined to be in the evaporated state, the electronic device 101 may apply the second current. For example, unless the liquid is determined to be in the evaporated state, the electronic device 101 may apply the first current. The electronic device 101 may apply the first current through a first pin (e.g., CC pin 721 or 722) of the USB type-C connector, determining whether the external electronic device 102 is connected to the connector.

According to an embodiment of the present disclosure, a method for preventing corrosion to a connector in an electronic device may comprise applying a first current to a first pin of the connector, determining whether liquid is introduced into the connector using a second pin of the connector, and when the liquid is introduced into the connector, applying a second current smaller than the first current to the first pin.

According to an embodiment of the present disclosure, the method may further comprise converting a value of an analog current passing through the second pin into a digital current value to determine whether the liquid introduced into the connector is evaporated, and when the liquid is evaporated, applying the first current to the first pin.

According to an embodiment of the present disclosure, the method may further comprise, upon determining that the liquid is not evaporated, maintaining the application of the second current to the first pin.

According to an embodiment of the present disclosure, the method may further comprise determining whether an interrupt occurs due to connection with an external electronic device via the connector, and upon determining that the connection with the external electronic device is made, applying the first current to the first pin.

According to an embodiment of the present disclosure, determining whether an interrupt occurs may include measuring a resistance based on a current applied through the second pin and determining that the interrupt occurs based on, at least, the measured resistance.

According to an embodiment of the present disclosure, the method may further comprise, when the measured resistance falls within a first range, determining that the liquid is a first liquid, and when the measured resistance falls within a second range, determining that the liquid is a second liquid.

According to an embodiment of the present disclosure, the first pin may be a CC pin, and the second pin may include at least one of a SBU pin, a GND pin, and a DET pin. The CC pin, the SBU pin, and the GND pin may be universal serial bus (USB) type-C pins, and the DET pin is a pin for detecting insertion of the external electronic device.

According to an embodiment of the present disclosure, the method may further comprise, upon determining that the liquid is introduced, providing information related to the introduction of the liquid through the display.

Figure 9:
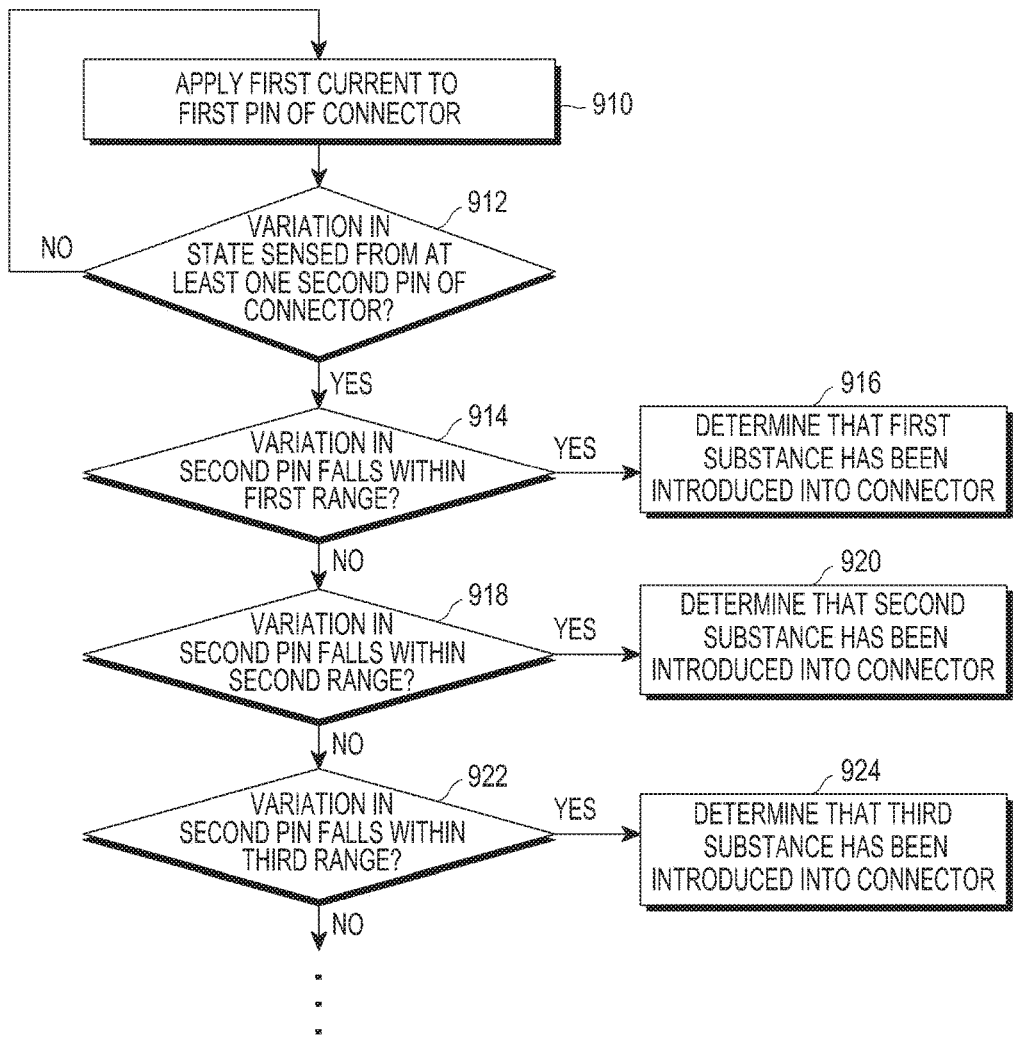
FIG. 9 is a flowchart illustrating operations for preventing corrosion in an electronic device according to an embodiment of the present disclosure.

FIG. 9 is a flowchart illustrating operations for preventing corrosion in an electronic device according to an embodiment of the present disclosure.

Referring to FIG. 9, in operation 910 the electronic device 101 (the processor 120 or the MCU 713) may apply a first current to a first pin of the connector. The electronic device 101 (the processor 120 or the MCU 713) may apply the first current through a CC pin of the USB type-C connector of the communication interface 170 to determine whether an external electronic device 102 is connected or a designated substance, e.g., liquid (or a foreign body), is introduced. The electronic device 101 (the processor 120 or the MCU 713) may apply the first current through a first pin (e.g., CC pin 721 or 722) of the USB type-C connector, determining whether the external electronic device 102 is connected or the designated substance is introduced. For example, the current may be about 100 μA. The magnitude of the first current may be variably be adjusted.

According to an embodiment of the present disclosure, in operation 912, the electronic device 101 (the processor 120 or the MCU 713) may detect a variation in the state of at least one pin of the connector. The electronic device 101 (the processor 120 or the MCU 713) may determine whether an interrupt occurs by detecting a variation in the state of at least one second pin (e.g., the SBU pin 723, GND pin 724, and the DET pin 725) of the USB type-C connector. The variation in state may include a variation in the magnitude of the current or voltage passing through the second pin or a variation in resistance. For example, when the electronic device 101 (the processor 120 or the MCU 713) applies the first current through the first pin (e.g., the CC pin 721 or 722) of the USB type-C connector and determines that the designated substance has been introduced, the electronic device 101 (the processor 120 or the MCU 713) may measure a resistance based on a current applied through at least one second pin (e.g., the SBU pin 723, GND pin 724, and the DET pin 725) of the USB type-C connector and determine the occurrence of an interrupt based on the measured resistance. For example, the electronic device 101 (the processor 120 or the MCU 713) may measure a resistance based on a voltage applied to the at least one second pin (e.g., the SBU pin 723, GND pin 724, and the DET pin 725) of the USB type-C connector, and the electronic device 101 (the processor 120 or the MCU 713) may determine the occurrence of an interrupt based on the measured resistance.

According to an embodiment of the present disclosure, in operation 914, the electronic device 101 (the processor 120 or the MCU 713) may determine whether a variation in the state of the second pin falls within a first range. The electronic device 101 (the processor 120 or the MCU 713) may determine whether a variation in the state (e.g., current, voltage, or resistance) of at least one second pin (e.g., the SBU pin 723, GND pin 724, and the DET pin 725) of the USB type-C connector falls within the first range. The first range may be varied depending on the target (e.g., current, voltage, or resistance) to be measured. The first range may be varied depending on the magnitude of the target (e.g., current, voltage, or resistance) to be measured. The range of each of the current, voltage, and resistance may be stored in the memory 130 of the electronic device 101.

According to an embodiment of the present disclosure, in operation 916, upon determining that the variation in the state of the at least one second pin falls within the first range, the electronic device 101 (the processor 120 or the MCU 713) may determine that a first substance has been introduced into the connector. Unless the variation in the state of the at least one second pin falls within the first range, the electronic device 101 (the processor 120 or the MCU 713) may determine that the first substance has not been introduced into the connector. According to an embodiment of the present disclosure, upon determining that the first substance has been introduced into the connector, the electronic device 101 may provide information about the introduction of the first substance to the user. For example, where the first substance is fresh water, information as to whether the fresh water has been introduced may be provided through the display of the electronic device to the user.

According to an embodiment of the present disclosure, in operation 918, the electronic device 101 (the processor 120 or the MCU 713) may determine whether a variation in the state of the second pin falls within a second range. The electronic device 101 (the processor 120 or the MCU 713) may determine whether a variation in the state (e.g., current, voltage, or resistance) of at least one second pin (e.g., the SBU pin 723, GND pin 724, and the DET pin 725) of the USB type-C connector falls within the second range. The second range may be varied depending on the target (e.g., current, voltage, or resistance) to be measured. The second range may be varied depending on the magnitude of the target (e.g., current, voltage, or resistance) to be measured. The range of each of the current, voltage, and resistance may be stored in the memory 130 of the electronic device 101.

According to an embodiment of the present disclosure, in operation 920, upon determining that the variation in the state of the at least one second pin falls within the second range, the electronic device 101 (the processor 120 or the MCU 713) may determine that a second substance has been introduced into the connector. Unless the variation in the state of the at least one second pin falls within the second range, the electronic device 101 (the processor 120 or the MCU 713) may determine that the second substance has not been introduced into the connector. According to an embodiment of the present disclosure, upon determining that the second substance has been introduced into the connector, the electronic device 101 may provide information about the introduction of the second substance to the user. For example, where the second substance is sea water (e.g., salt-containing fresh water), information as to whether sea water has been introduced and a notification to let the user rinse off the salt water and dry the electronic device to prevent corrosion to the electronic device (e.g., the pins of the connector) may be provided through the display of the electronic device to the user.

According to an embodiment of the present disclosure, in operation 922, the electronic device 101 (the processor 120 or the MCU 713) may determine whether a variation in the state of the second pin falls within a third range. The electronic device 101 (the processor 120 or the MCU 713) may determine whether a variation in the state (e.g., current, voltage, or resistance) of at least one second pin (e.g., the SBU pin 723, GND pin 724, and the DET pin 725) of the USB type-C connector falls within the third range. The third range may be varied depending on the target (e.g., current, voltage, or resistance) to be measured. The third range may be varied depending on the magnitude of the target (e.g., current, voltage, or resistance) to be measured. The range of each of the current, voltage, and resistance may be stored in the memory 130 of the electronic device 101.

According to an embodiment of the present disclosure, in operation 924, upon determining that the variation in the state of the at least one second pin falls within the third range, the electronic device 101 (the processor 120 or the MCU 713) may determine that a third substance has been introduced into the connector. Unless the variation in the state of the at least one second pin falls within the third range, the electronic device 101 (the processor 120 or the MCU 713) may determine that the third substance has not been introduced into the connector. According to an embodiment of the present disclosure, upon determining that the third substance has been introduced into the connector, the electronic device 101 may provide information about the introduction of the third substance to the user. For example, where the third substance is sugar-containing water (e.g., Coke), information as to whether the third substance has been introduced and a notification to let the user rinse off the third substance and dry the electronic device to prevent corrosion to the electronic device (e.g., the pins of the connector) may be provided through the display of the electronic device to the user.

According to an embodiment of the present disclosure, the first range, the second range, and the third range may be varied depending on the type of the substance introduced into the connector or the concentration of the different substance contained in the substance. For example, where the different substance is salt (or sugar), the first range may have a lowest salt (or sugar) concentration, the second range may have a salt (or sugar) concentration higher than the first range, and the third range may have a salt (or sugar) concentration higher than the second range. Alternatively, the first range may have a highest salt (or sugar) concentration, the second range may have a salt (or sugar) concentration lower than the first range, and the third range may have a salt (or sugar) concentration lower than the second range.

According to an embodiment of the present disclosure, a method for preventing corrosion to a connector of an electronic device may comprise connecting with an external electronic device via the connector including at least one pin capable of detecting a contact of a designated substance and detecting whether at least part of the designated substance contains a substance different from the designated substance through the at least one pin.

According to an embodiment of the present disclosure, the method may further comprise providing first information through the display when a substance detected through a detecting circuit for detecting whether at least part of the designated substance contains a substance different from the designated substance is the designated substance and providing second information through the display when the substance detected through the detecting circuit is the different substance.

According to an embodiment of the present disclosure, the method may further comprise measuring a resistance based on a current applied through the at least one pin, determining that the detected substance is the designated substance when the measured resistance falls within a first range, and determining that the detected substance is the substance containing the different substance when the measured resistance falls within a second range.

According to an embodiment of the present disclosure, the method may further comprise cutting off a current to the at least one other pin upon detecting the designated substance or the substance containing the different substance through the detecting circuit.

The term 'module' may refer to a unit including one of hardware, software, and firmware, or a combination thereof. The term 'module' may be interchangeably used with a unit, logic, logical block, component, or circuit. The module may be a minimum unit or part of an integrated component. The module may be a minimum unit or part of performing one or more functions. The module may be implemented mechanically or electronically. For example, the module as used herein may include at least one of application specific integrated circuit (ASIC) chips, field programmable gate arrays (FPGAs), or programmable logic arrays (PLAs) that perform some operations, which have already been known or will be developed in the future.

According to an embodiment of the present disclosure, at least a part of the device (e.g., modules or their functions) or method (e.g., operations) may be implemented as instructions stored in a computer-readable storage medium e.g., in the form of a programming module. When the instructions are executed by a control circuit, the control circuit may perform functions corresponding to the instructions. The computer-readable storage medium may be e.g., the memory 130. At least a part of the programming module may be implemented (e.g., executed) by e.g., a control circuit. At least part of the programming module may include e.g., a module, program, routine, set of instructions, process, or the like for performing one or more functions.

The computer-readable recording medium may include a magnetic medium, such as a hard disk, a floppy disk, and a magnetic tape, an optical recording medium, such as a compact disc-read only memory (CD-ROM) or DVD, a magnetic-optical medium, such as a floptical disc, and a hardware device specially configured to store and execute program instructions (e.g., a programming module), such as a read only memory (ROM), random access memory (RAM), or flash memory. Examples of the program commands may include not only machine language codes but also high-level language codes which are executable by various computing means using an interpreter. The aforementioned hardware devices may be configured to operate as one or more software modules to carry out embodiments of the present disclosure, and vice versa.

Modules or programming modules in accordance with various embodiments of the present disclosure may include at least one or more of the aforementioned components, omit some of them, or further include other additional components. Operations performed by modules, programming modules or other components in accordance with various embodiments of the present disclosure may be carried out sequentially, simultaneously, repeatedly, or heuristically. Furthermore, some of the operations may be performed in a different order, or omitted, or include other additional operation(s). According to an embodiment of the present disclosure, there may be provided a storage medium storing commands. The commands may include a first command set for applying a first current to a first pin of a connector of an electronic device in a method for preventing corrosion to the connector of the electronic device, a second command set for determining whether liquid is introduced into the connector using a second pin of the connector, and a third command set for applying a second current smaller than the first current to the first pin when the liquid is introduced into the connector.

As is apparent from the foregoing description, according to the embodiments of the present disclosure, when a foreign body (e.g., liquid) is introduced into the connector, the magnitude of the current steadily supplied may be controlled, preventing corrosion to the connector and enhancing the stability of the electronic device.

According to the embodiments of the present disclosure, a resistance caused by a foreign body may be measured, providing for the determination of the type of the foreign body.

While the present disclosure has been shown and described with reference to various embodiments thereof, it will be understood by those skilled in the art that various changes in form or detail may be made therein without departing from the spirit and scope of the present disclosure as defined by the appended claims and their equivalents.

What is claimed is:
1. An electronic device comprising:
a connector configured to include a first pin and a second pin;
a communication interface connected with the connector; and
at least one processor electrically connected with the communication interface, wherein the at least one processor is configured to:
apply, to the first pin, a first current for identifying a connection with a first external electronic device,
detect a current passing through the second pin,
determine whether liquid is introduced into the connector based on the detected current, and
based on determining that the liquid is introduced into the connector, apply, to the first pin, a second current adjusted from the first current for preventing corrosion of the connector,
wherein the second current is smaller than the first current.

2. The electronic device of claim 1, wherein the at least one processor is further configured to:
convert a value of an analog current passing through the second pin into a digital current value to determine whether the liquid introduced into the connector is evaporated, and
based on determining that the liquid is evaporated, apply the first current to the first pin.

3. The electronic device of claim 2, wherein, based on determining that the liquid is not evaporated, the at least one processor is further configured to maintain the applying of the second current to the first pin.

4. The electronic device of claim 1, wherein the at least one processor is further configured to:
determine whether an interrupt occurs due to the connection with the first external electronic device via the connector, and
based on determining that the interrupt occurs due to the connection with the first external electronic device, apply the first current to the first pin.

5. The electronic device of claim 1, wherein the at least one processor is further configured to:
measure a resistance based on the detected current, and
determine that an interrupt occurs based on, at least, the measured resistance.

6. The electronic device of claim 1, wherein the at least one processor is further configured to measure a resistance based on the detected current, and
determine a type of the liquid based on the measured resistance.

7. The electronic device of claim 1,
wherein the first pin is a configuration channel (CC) pin,
wherein the second pin includes at least one of a secondary bus (SBU) pin, a ground (GND) pin, or a detection (DET) pin,
wherein the CC pin, the SBU pin, and the GND pin are universal serial bus (USB) type-C pins, and
wherein the DET pin is a pin for detecting insertion of the first external electronic device.

8. The electronic device of claim 1, further comprising a display,
wherein, based on determining that the liquid is introduced, the at least one processor is further configured to provide information that the liquid is introduced through the display.

9. The electronic device of claim 1, further comprising a camera,
wherein the at least one processor is further configured to:
determine that the liquid is present inside the connector for a predetermined time based on the detected current, and
based on determining that the liquid is present inside the connector for the predetermined time, execute an underwater photography mode of the camera.

10. The electronic device of claim 1, wherein the at least one processor is further configured to cut off the second current to the first pin based on determining that the liquid is introduced.

11. The electronic device of claim 1, further comprising a communication circuit,
wherein the at least one processor is further configured to:
determine that the liquid is present inside the connector for a predetermined time based on the detected current,
based on determining that the liquid is present inside the connector for the predetermined time, obtain, by using the communication circuit, geographical information of the electronic device, and
control the communication circuit to transmit a signal including the obtained geographical information to a second external electronic device.

12. A method for preventing corrosion to a connector in an electronic device, the method comprising:
applying, to a first pin of the connector, a first current for identifying a connection with a first external electronic device;
detecting a current passing through a second pin of the connector;
determining whether liquid is introduced into the connector based on the detected current; and
based on determining that the liquid is introduced into the connector, applying, to the first pin, a second current adjusted from the first current for preventing corrosion of the connector,
wherein the second current is smaller than the first current.

13. The method of claim 12, further comprising:
converting a value of an analog current passing through the second pin into a digital current value to determine whether the liquid introduced into the connector is evaporated; and
based on determining that the liquid is evaporated, applying the first current to the first pin.

14. The method of claim 13, further comprising, based on determining that the liquid is not evaporated, maintaining applying of the second current to the first pin.

15. The method of claim 12, further comprising:
determining whether an interrupt occurs due to the connection with the first external electronic device via the connector; and
based on determining that the interrupt occurs due to the connection with the first external electronic device, applying the first current to the first pin.

16. The method of claim 12, further comprising:
measuring a resistance based on the detected current; and
determining that an interrupt occurs based on, at least, the measured resistance.

17. The method of claim 12, further comprising:
measuring a resistance based on the detected current, and
determining a type of the liquid based on the measured resistance.

* * * * *